(12) United States Patent
Monia et al.

(10) Patent No.: US 8,389,488 B2
(45) Date of Patent: Mar. 5, 2013

(54) ANTIDOTES TO ANTISENSE COMPOUNDS

(75) Inventors: Brett P. Monia, Encinitas, CA (US); Andrew M. Siwkowski, Carlsbad, CA (US); Hong Zhang, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 41 days.

(21) Appl. No.: 12/740,974

(22) PCT Filed: Nov. 5, 2008

(86) PCT No.: PCT/US2008/082511
§ 371 (c)(1),
(2), (4) Date: Sep. 13, 2010

(87) PCT Pub. No.: WO2009/061841
PCT Pub. Date: May 14, 2009

(65) Prior Publication Data
US 2010/0331392 A1   Dec. 30, 2010

Related U.S. Application Data

(60) Provisional application No. 60/985,595, filed on Nov. 5, 2007.

(51) Int. Cl.
| | |
|---|---|
| *A61K 48/00* | (2006.01) |
| *C12N 15/11* | (2006.01) |
| *C07H 21/02* | (2006.01) |
| *C07H 21/04* | (2006.01) |

(52) U.S. Cl. ................................ 514/44 A; 536/24.5
(58) Field of Classification Search ............ 514/44; 536/24.5
See application file for complete search history.

(56) References Cited

FOREIGN PATENT DOCUMENTS

| | | |
|---|---|---|
| WO | WO 02/059137 | 8/2002 |
| WO | WO 02/096926 | 12/2002 |
| WO | WO 2004/027030 | 4/2004 |
| WO | WO 2004/063329 | 7/2004 |
| WO | WO 2008/066621 | 6/2008 |
| WO | WO 2009/045545 | 9/2009 |

OTHER PUBLICATIONS

International Search Report for application PCT/US2008/082511 dated Jun. 16, 2009.

*Primary Examiner* — Terra Cotta Gibbs
(74) *Attorney, Agent, or Firm* — Knobbe, Martens, Olson & Bear

(57) ABSTRACT

The present invention relates to antisense antidote compounds and uses thereof. Such antidote compounds reduce the magnitude and/or duration of the antisense activity of an antisense compound.

18 Claims, 10 Drawing Sheets

ANTIDOTES TO ANTISENSE COMPOUNDS

RELATED APPLICATIONS

This application is a 35 U.S.C. §371 national phase application of international application serial no. PCT/US2008/082511, filed on Nov. 5, 2008, which is a non-provisional of U.S. patent application Ser. No. 60/985,595, filed on Nov. 5, 2007, the disclosure of each of which is incorporated herein by reference in its entirety.

SEQUENCE LISTING

The present application is being filed along with a Sequence Listing in electronic format. The Sequence Listing is provided as a file entitled CORE0076WOSEQ.txt, created Nov. 5, 2007, which is 4.0 Kb in size. The information in the electronic format of the sequence listing is incorporated herein by reference in its entirety.

FIELD OF THE INVENTION

The present invention provides methods and compositions for modulating antisense activity.

BACKGROUND OF THE INVENTION

Antisense compounds have been used to modulate target nucleic acids. Antisense compounds comprising a variety of modifications and motifs have been reported. In certain instances, such compounds are useful as research tools and as therapeutic agents.

SUMMARY OF THE INVENTION

In certain embodiments, provided herein are antidote compounds. Such compounds reduce antisense activity of an antisense compound. In certain embodiments, the present invention provides antidote compounds that are complementary to antisense compounds.

In certain embodiments, the present invention provides antidote compounds comprising a modified oligonucleotide consisting of 12 to 30 linked nucleosides and having a nucleobase sequence complementary to an antisense compound. In certain such embodiments, the modified oligonucleotide is a single-stranded oligonucleotide and/or is at least 90% complementary to the antisense compound. In certain embodiments, the antidote compound is fully complementary to the antisense compound.

In certain embodiments, antidote compounds at least one internucleoside linkage of an antidote compound is a modified internucleoside linkage. In certain such embodiments, at least one internucleoside linkage is a phosphorothioate internucleoside linkage.

In certain embodiments, antidote compounds comprise at least one nucleoside comprising a modified sugar. In certain such embodiments, the modified sugar is a bicyclic sugar or sugar comprising a 2'-O-methoxyethyl.

In certain embodiments, antidote compounds comprise at least one nucleoside comprising a modified nucleobase. In certain such embodiments, the modified nucleobase is a 5-methylcytosine.

In certain embodiments, antidote compounds comprise at least one modification. In certain such embodiments, antidote compounds comprise one or more nucleoside modifications and or one or more linkage modifications. In certain embodiments, antidote compounds comprise one or more modifications selected from: sugar modifications, linkage modifications and nucleobase modifications.

In certain embodiments, antidote compounds comprise a modified oligonucleotide comprising: a gap segment consisting of linked deoxynucleosides; a 5' wing segment consisting of linked nucleosides; a 3' wing segment consisting of linked nucleosides; wherein the gap segment is positioned between the 5' wing segment and the 3' wing segment and wherein each nucleoside of each wing segment comprises a modified sugar.

In certain embodiments, antidote compounds comprise a modified oligonucleotide comprising: a gap segment consisting of ten linked deoxynucleosides; a 5' wing segment consisting of five linked nucleosides; a 3' wing segment consisting of five linked nucleosides; wherein the gap segment is positioned between the 5' wing segment and the 3' wing segment, wherein each nucleoside of each wing segment comprises a 2'-O-methoxyethyl sugar; and wherein each internucleoside linkage is a phosphorothioate linkage.

In certain embodiments, antidote compound of any of the above claims, comprise a modified oligonucleotide consisting of 20 linked nucleosides.

In certain embodiments, antidote compound comprise a modified oligonucleotide wherein each nucleoside is modified.

In certain embodiments, antidote compounds are complementary to an antisense compound, wherein the antisense compound is targeted to an mRNA. In certain embodiments, the antisense compound is targeted to an mRNA encoding a blood factor. In certain embodiments, the antisense compound is targeted to an mRNA encoding a protein involved in metabolism. In certain embodiments, the antisense compound is targeted to an mRNA encoding a protein involved in diabetes. In certain embodiments, the antisense compound is targeted to an mRNA encoding a protein involved in cardiopathology. In certain embodiments, the antisense compound is targeted to an mRNA encoding a protein expressed in nerve cells. In certain embodiments, the antisense compound is targeted to an mRNA encoding a protein expressed in the central nervous system. In certain embodiments, the antisense compound is targeted to an mRNA expressed in peripheral nerves.

In certain embodiments, the antisense compound is targeted to an mRNA encoding a protein expressed in the liver. In certain embodiments, the antisense compound is targeted to an mRNA encoding a protein expressed in the kidney.

In certain embodiments, the antisense compound is targeted to a pre-mRNA. In certain embodiments, the antisense compound is targeted to a micro-RNA. In certain embodiments, the antisense compound is an RNase H dependent antisense compound. In certain embodiments, the antisense compound alters splicing of a target nucleic acid. In certain embodiments, the antisense compound activates the RISC pathway.

In certain embodiments, antidote compounds activate RNase H. certain embodiments, antidote compounds activate the RISC pathway.

In certain embodiments, the invention provides a composition comprising an antidote compound or a salt thereof and a pharmaceutically acceptable carrier or diluent.

In certain embodiments, the invention provides methods comprising administering to an animal an antidote compound or composition. In certain embodiments, the animal is a human. In certain embodiments, the administering is oral, topical, or parenteral.

In certain embodiments, the invention provides methods of inhibiting antisense activity in a cell comprising contacting the cell with an antidote compound according the present invention and thereby inhibiting the antisense activity in the cell. In certain such embodiments, the cell is in an animal. In certain embodiments, the animal is a human.

In certain embodiments, the invention provides methods comprising: contacting a cell with an antisense compound; detecting antisense activity; and contacting the cell with an antidote compound. In certain embodiments, the method the detecting antisense activity comprises measuring the amount of target mRNA present, the amount of target protein present, and/or the activity of a target protein. In certain embodiments, such methods comprising detecting antidote activity by measuring antisense activity after contacting the cell with antidote compound. In certain such methods, the cell is in an animal. In certain embodiments, the animal is a human.

In certain embodiments, the invention provides methods of ameliorating a side-effect of antisense treatment comprising: contacting a cell with an antisense compound; detecting a side-effect; contacting the cell with an antidote compound; and thereby ameliorating the side effect of the antisense compound.

In certain embodiments, the invention provides methods of treating a patient comprising: administering to the patient an antisense compound; monitoring the patient for antisense activity; and if the antisense activity becomes higher than desired, administrating an antidote compound. In certain such embodiments, the monitoring antisense activity comprises measuring the amount of target mRNA present, measuring the amount of target protein present and/or measuring the activity of a target protein. In certain embodiments, such methods include detecting antidote activity by measuring antisense activity after administration of the antidote compound. In certain embodiments, the patient is a human.

In certain embodiments, the invention provides methods of treating a patient comprising: administering to the patient an antisense compound; monitoring the patient for one or more side effect; and if the one or more side effect reaches an undesirable level, administrating an antidote compound. In certain such embodiments, the patient is a human.

In certain embodiments, the invention provides a kit comprising an antisense compound and an antidote compound; an antidote compound and a non-oligomeric antidote; or an antisense compound, an antidote compound, and a non-oligomeric antidote. In certain such embodiments, the non-oligomeric antidote is a target protein.

DETAILED DESCRIPTION OF THE INVENTION

Figure 1:
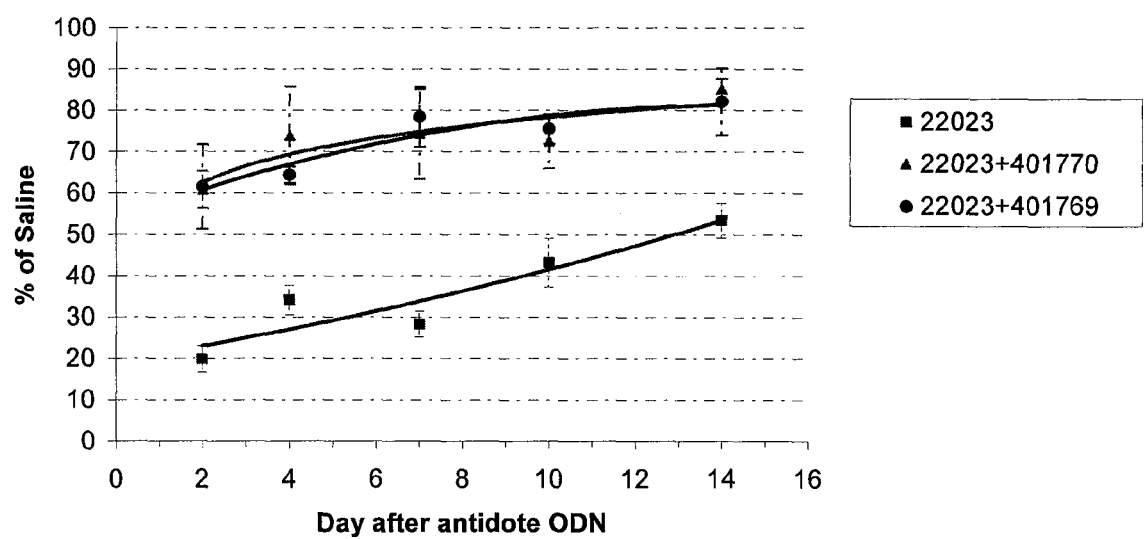
FIG. 1 shows Fas RNA levels in livers of mice after antisense treatment with and without subsequent antidote treatment as discussed in Example 3. Results are expressed as percent of control mice.

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

DEFINITIONS

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 18th edition, 1990; and "Antisense Drug Technology, Principles, Strategies, and Applications" Edited by Stanley T. Crooke, CRC Press, Boca Raton, Fla.; and Sambrook et al., "Molecular Cloning, A laboratory Manual," $2^{nd}$ Edition, Cold Spring Harbor Laboratory Press, 1989, which are hereby incorporated by reference for any purpose. Where permitted, all patents, applications, published applications and other publications and other data referred to throughout in the disclosure herein are incorporated by reference in their entirety.

Unless otherwise indicated, the following terms have the following meanings:

As used herein, the term "nucleoside" means a glycosylamine comprising a nucleobase and a sugar. Nucleosides includes, but are not limited to, naturally occurring nucleosides, abasic nucleosides, modified nucleosides, and nucleosides having mimetic bases and/or sugar groups.

As used herein, the term "nucleotide" refers to a glycosomine comprising a nucleobase and a sugar having a phosphate group covalently linked to the sugar. Nucleotides may be modified with any of a variety of substituents.

As used herein, the term "nucleobase" refers to the base portion of a nucleoside or nucleotide. A nucleobase may comprise any atom or group of atoms capable of hydrogen bonding to a base of another nucleic acid.

As used herein, the term "heterocyclic base moiety" refers to a nucleobase comprising a heterocycle.

As used herein, the term "oligomeric compound" refers to a polymeric structure comprising two or more sub-structures and capable of hybridizing to a region of a nucleic acid molecule. In certain embodiments, oligomeric compounds are oligonucleosides. In certain embodiments, oligomeric compounds are oligonucleotides. In certain embodiments, oligomeric compounds are antisense compounds. In certain embodiments, oligomeric compounds are antidote compounds. In certain embodiments, oligomeric compounds comprise conjugate groups.

As used herein "oligonucleoside" refers to an oligonucleotide in which the internucleoside linkages do not contain a phosphorus atom.

As used herein, the term "oligonucleotide" refers to an oligomeric compound comprising a plurality of linked nucleosides. In certain embodiment, one or more nucleotides of an oligonucleotide is modified. In certain embodiments, an oligonucleotide comprises ribonucleic acid (RNA) or deoxyribonucleic acid (DNA). In certain embodiments, oligonucleotides are composed of naturally- and/or non-naturally-occurring nucleobases, sugars and covalent internucleoside linkages, and may further include non-nucleic acid conjugates.

As used herein "internucleoside linkage" refers to a covalent linkage between adjacent nucleosides.

As used herein "naturally occurring internucleoside linkage" refers to a 3' to 5' phosphodiester linkage.

As used herein, the term "antisense compound" refers to an oligomeric compound that is at least partially complementary to a target nucleic acid molecule to which it hybridizes. In certain embodiments, an antisense compound modulates (increases or decreases) expression or amount of a target nucleic acid. In certain embodiments, an antisense compound alters splicing of a target pre-mRNA resulting in a different splice variant. Antisense compounds include, but are not limited to, compounds that are oligonucleotides, oligonucleosides, oligonucleotide analogs, oligonucleotide mimetics, and chimeric combinations of these. Consequently, while all antisense compounds are oligomeric compounds, not all oligomeric compounds are antisense compounds.

As used herein, the term "antisense oligonucleotide" refers to an antisense compound that is an oligonucleotide.

As used herein, the term "antisense activity" refers to any detectable and/or measurable activity attributable to the hybridization of an antisense compound to its target nucleic acid. Such detection and or measuring may be direct or indirect. For example, in certain embodiments, antisense activity is assessed by detecting and or measuring the amount of target protein. In certain embodiments, antisense activity is assessed by detecting and/or measuring the amount of target nucleic acids and/or cleaved target nucleic acids and/or alternatively spliced target nucleic acids.

As used herein the term "detecting antisense activity" or "measuring antisense activity" means that a test for detecting or measuring antisense activity is performed on a particular sample and compared to that of a control sample. Such detection and/or measuring may include values of zero. Thus, if a test for detection of antisense activity results in a finding of no antisense activity (antisense activity of zero), the step of "detecting antisense activity" has nevertheless been performed.

As used herein the term "control sample" refers to a sample that has not been contacted with a reporter oligomeric compound.

As used herein, the term "motif" refers to the pattern of unmodified and modified nucleotides in an oligomeric compound.

As used herein, the term "antidote compound" refers to an oligomeric compound that is complementary to and capable of hybridizing with an antisense compound.

As used herein, the term "non-oligomeric antidote" refers to a compound that does not hybridize with an antisense compound and that reduces the amount or duration of an antisense activity. In certain embodiments, a non-oligomeric antidote is a target protein.

As used herein, the term "antidote activity" refers to any decrease in intensity or duration of any antisense activity attributable to hybridization of an antidote compound to an antisense compound.

As used herein, the term "chimeric antisense oligomer" refers to an antisense oligomeric compound, having at least one sugar, nucleobase or internucleoside linkage that is differentially modified as compared to at least on other sugar, nucleobase or internucleoside linkage within the same antisense oligomeric compound. The remainder of the sugars, nucleobases and internucleoside linkages can be independently modified or unmodified, the same or different.

As used herein, the term "chimeric antisense oligonucleotide" refers to an antisense oligonucleotide, having at least one sugar, nucleobase or internucleoside linkage that is differentially modified as compared to at least on other sugar, nucleobase or internucleoside linkage within the same antisense oligonucleotide. The remainder of the sugars, nucleobases and internucleoside linkages can be independently modified or unmodified, the same or different.

As used herein, the term "mixed-backbone oligomeric compound" refers to an oligomeric compound wherein at least one internucleoside linkage of the oligomeric compound is different from at least one other internucleoside linkage of the oligomeric compound.

As used herein, the term "target protein" refers to a protein, the modulation of which is desired.

As used herein, the term "target gene" refers to a gene encoding a target protein.

As used herein, the term "target nucleic acid" refers to any nucleic acid molecule the expression or activity of which is capable of being modulated by an antisense compound. Target nucleic acids include, but are not limited to, RNA (including, but not limited to pre-mRNA and mRNA or portions thereof) transcribed from DNA encoding a target protein, and also cDNA derived from such RNA, and miRNA. For example, the target nucleic acid can be a cellular gene (or mRNA transcribed from the gene) whose expression is associated with a particular disorder or disease state, or a nucleic acid molecule from an infectious agent.

As used herein, the term "target antisense compound" refers to an antisense compound that is targeted by an antidote compound.

As used herein, the term "targeting" or "targeted to" refers to the association of an antisense compound to a particular target nucleic acid molecule or a particular region of nucleotides within a target nucleic acid molecule.

As used herein, the term "nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

As used herein, the term "non-complementary nucleobase" refers to a pair of nucleobases that do not form hydrogen bonds with one another or otherwise support hybridization.

As used herein, the term "complementary" refers to the capacity of an oligomeric compound to hybridize to another oligomeric compound or nucleic acid through nucleobase complementarity. In certain embodiments, an antisense compound and its target are complementary to each other when a sufficient number of corresponding positions in each molecule are occupied by nucleobases that can bond with each other to allow stable association between the antisense compound and the target. One skilled in the art recognizes that the inclusion of mismatches is possible without eliminating the ability of the oligomeric compounds to remain in association. Therefore, described herein are antisense compounds that may comprise up to about 20% nucleotides that are mismatched (i.e., are not nucleobase complementary to the corresponding nucleotides of the target). Preferably the antisense compounds contain no more than about 15%, more preferably not more than about 10%, most preferably not more than 5% or no mismatches. The remaining nucleotides are nucleobase complementary or otherwise do not disrupt hybridization (e.g., universal bases). One of ordinary skill in the art would recognize the compounds provided herein are at least 80%, at least 85%, at least 90%, at least 95%, at least 96%, at least 97%, at least 98%, at least 99% or 100% complementary to a target nucleic acid.

As used herein, "hybridization" means the pairing of complementary oligomeric compounds (e.g., an antisense compound and its target nucleic acid or an antidote to its antisense compound). While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is nucleobase complementary to the natural nucleobases thymidine and uracil which pair through the formation of hydrogen bonds. The natural base guanine is nucleobase complementary to the natural bases cytosine and 5-methyl cytosine. Hybridization can occur under varying circumstances.

As used herein, the term "specifically hybridizes" refers to the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "designing" or "designed to" refer to the process of designing an oligomeric compound that specifically hybridizes with a selected nucleic acid molecule.

As used herein, the term "modulation" refers to a perturbation of function or activity when compared to the level of the function or activity prior to modulation. For example, modulation includes the change, either an increase (stimulation or induction) or a decrease (inhibition or reduction) in gene expression. As further example, modulation of expression can include perturbing splice site selection of pre-mRNA processing.

As used herein, the term "expression" refers to all the functions and steps by which a gene's coded information is converted into structures present and operating in a cell. Such structures include, but are not limited to the products of transcription and translation.

As used herein, "variant" refers to an alternative RNA transcript that can be produced from the same genomic region of DNA. Variants include, but are not limited to "pre-mRNA variants" which are transcripts produced from the same genomic DNA that differ from other transcripts produced from the same genomic DNA in either their start or stop position and contain both intronic and exonic sequence. Variants also include, but are not limited to, those with alternate splice junctions, or alternate initiation and termination codons.

As used herein, "high-affinity modified monomer" refers to a monomer having at least one modified nucleobase, internucleoside linkage or sugar moiety, when compared to naturally occurring monomers, such that the modification increases the affinity of an antisense compound comprising the high-affinity modified monomer to its target nucleic acid. High-affinity modifications include, but are not limited to, monomers (e.g., nucleosides and nucleotides) comprising 2'-modified sugars.

As used herein, the term "2'-modified" or "2'-substituted" means a sugar comprising substituent at the 2' position other than H or OH. 2'-modified monomers, include, but are not limited to, BNA's and monomers (e.g., nucleosides and nucleotides) with 2'-substituents, such as allyl, amino, azido, thio, O-allyl, O—C1-C10 alkyl, —OCF3, O—(CH2)2-O—CH3, 2'-O(CH2)2SCH3, O—(CH2)2-O—N(Rm)(Rn), or O—CH2-C(=O)—N(Rm)(Rn), where each Rm and Rn is, independently, H or substituted or unsubstituted C1-C10 alkyl. In certain embodiments, oligomeric compounds comprise a 2' modified monomer that does not have the formula 2'-O(CH2)nH, wherein n is one to six. In certain embodiments, oligomeric compounds comprise a 2' modified monomer that does not have the formula 2'-OCH3. In certain embodiments, oligomeric compounds comprise a 2' modified monomer that does not have the formula or, in the alternative, 2'-O(CH2)2OCH3.

As used herein, the term "bicyclic nucleic acid" or "BNA" or "bicyclic nucleoside" or "bicyclic nucleotide" refers to a nucleoside or nucleotide wherein the furanose portion of the nucleoside includes a bridge connecting two carbon atoms on the furanose ring, thereby forming a bicyclic ring system.

As used herein, unless otherwise indicated, the term "methyleneoxy BNA" alone refers to β-D-methyleneoxy BNA.

As used herein, the term "MOE" refers to a 2'-O-methoxyethyl substituent.

As used herein, the term "gapmer" refers to a chimeric oligomeric compound comprising a central region (a "gap") and a region on either side of the central region (the "wings"), wherein the gap comprises at least one modification that is different from that of each wing. Such modifications include nucleobase, monomeric linkage, and sugar modifications as well as the absence of modification (unmodified). Thus, in certain embodiments, the nucleotide linkages in each of the wings are different than the nucleotide linkages in the gap. In certain embodiments, each wing comprises nucleotides with high affinity modifications and the gap comprises nucleotides that do not comprise that modification. In certain embodiments the nucleotides in the gap and the nucleotides in the wings all comprise high affinity modifications, but the high affinity modifications in the gap are different than the high affinity modifications in the wings. In certain embodiments, the modifications in the wings are the same as one another. In certain embodiments, the modifications in the wings are different from each other. In certain embodiments, nucleotides in the gap are unmodified and nucleotides in the wings are modified. In certain embodiments, the modification(s) in each wing are the same. In certain embodiments, the modification(s) in one wing are different from the modification(s) in the other wing. In certain embodiments, oligomeric compounds are gapmers having 2'-deoxynucleotides in the gap and nucleotides with high-affinity modifications in the wing.

As used herein, the term "prodrug" refers to a therapeutic agent that is prepared in an inactive form that is converted to an active form (i.e., drug) within the body or cells thereof by the action of endogenous enzymes or other chemicals and/or conditions.

As used herein, the term "pharmaceutically acceptable salts" refers to salts of active compounds that retain the desired biological activity of the active compound and do not impart undesired toxicological effects thereto.

As used herein, the term "cap structure" or "terminal cap moiety" refers to chemical modifications, which have been incorporated at either terminus of an antisense compound.

As used herein, the term "prevention" refers to delaying or forestalling the onset or development of a condition or disease for a period of time from hours to days, preferably weeks to months.

As used herein, the term "amelioration" refers to a lessening of at least one activity or one indicator of the severity of a condition or disease. The severity of indicators may be determined by subjective or objective measures which are known to those skilled in the art.

As used herein, the term "treatment" refers to administering a composition of the invention to effect an alteration or improvement of the disease or condition. Prevention, amelioration, and/or treatment may require administration of multiple doses at regular intervals, or prior to onset of the disease or condition to alter the course of the disease or condition. Moreover, a single agent may be used in a single individual for each prevention, amelioration, and treatment of a condition or disease sequentially, or concurrently.

As used herein, the term "pharmaceutical agent" refers to a substance that provides a therapeutic benefit when administered to a subject. In certain embodiments, a pharmaceutical agent is an active pharmaceutical agent. In certain embodiments, a pharmaceutical agent is a prodrug.

As used herein, the term "therapeutically effective amount" refers to an amount of a pharmaceutical agent that provides a therapeutic benefit to an animal.

As used herein, "administering" means providing a pharmaceutical agent to an animal, and includes, but is not limited to administering by a medical professional and self-administering.

As used herein, the term "co-administering" means providing more than one pharmaceutical agent to an animal. In certain embodiments, such more than one pharmaceutical agents are administered together. In certain embodiments, such more than one pharmaceutical agents are administered separately. In certain embodiments, such more than one pharmaceutical agents are administered at the same time. In certain embodiments, such more than one pharmaceutical agents are administered at different times. In certain embodiments, such more than one pharmaceutical agents are administered through the same route of administration. In certain embodiments, such more than one pharmaceutical agents are administered through different routes of administration. In certain embodiments, such more than one pharmaceutical agents are contained in the same pharmaceutical formulation. In certain embodiments, such more than one pharmaceutical agents are in separate formulations.

As used herein, the term "pharmaceutical composition" refers to a mixture of substances suitable for administering to an individual. For example, a pharmaceutical composition may comprise an antisense oligonucleotide and a sterile aqueous solution. In certain embodiments, a pharmaceutical composition includes a pharmaceutical agent and a diluent and/or carrier.

As used herein, the term "animal" refers to a human or non-human animal, including, but not limited to, mice, rats, rabbits, dogs, cats, pigs, and non-human primates, including, but not limited to, monkeys and chimpanzees.

As used herein, the term "parenteral administration," refers to administration through injection or infusion. Parenteral administration includes, but is not limited to, subcutaneous administration, intravenous administration, or intramuscular administration.

As used herein, the term "subcutaneous administration" refers to administration just below the skin. "Intravenous administration" means administration into a vein.

As used herein, the term "dose" refers to a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

As used herein, the term "dosage unit" refers to a form in which a pharmaceutical agent is provided. In certain embodiments, a dosage unit is a vial comprising lyophilized antisense oligonucleotide. In certain embodiments, a dosage unit is a vial comprising reconstituted antisense oligonucleotide.

As used herein, the term "active pharmaceutical ingredient" refers to the substance in a pharmaceutical composition that provides a desired effect.

As used herein, the term "side effects" refers to physiological responses attributable to a treatment other than desired effects. In certain embodiments, side effects include, without limitation, injection site reactions, liver function test abnormalities, renal function abnormalities, liver toxicity, renal toxicity, central nervous system abnormalities, and myopathies. For example, increased aminotransferase levels in serum may indicate liver toxicity or liver function abnormality. For example, increased bilirubin may indicate liver toxicity or liver function abnormality.

As used herein, the term "alkyl," as used herein, refers to a saturated straight or branched hydrocarbon radical containing up to twenty four carbon atoms. Examples of alkyl groups include, but are not limited to, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms (C1-C12 alkyl) with from 1 to about 6 carbon atoms being more preferred. The term "lower alkyl" as used herein includes from 1 to about 6 carbon atoms. Alkyl groups as used herein may optionally include one or more further substituent groups.

As used herein, the term "alkenyl," as used herein, refers to a straight or branched hydrocarbon chain radical containing up to twenty four carbon atoms and having at least one carbon-carbon double bond. Examples of alkenyl groups include, but are not limited to, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, the term "alkynyl," as used herein, refers to a straight or branched hydrocarbon radical containing up to twenty four carbon atoms and having at least one carbon-carbon triple bond. Examples of alkynyl groups include, but are not limited to, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, the term "aminoalkyl" as used herein, refers to an amino substituted alkyl radical. This term is meant to include C1-C12 alkyl groups having an amino substituent at any position and wherein the alkyl group attaches the aminoalkyl group to the parent molecule. The alkyl and/or amino portions of the aminoalkyl group can be further substituted with substituent groups.

As used herein, the term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines. Aliphatic groups as used herein may optionally include further substituent groups.

As used herein, the term "alicyclic" or "alicyclyl" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups. As used herein, the term "alkoxy," as used herein, refers to a radical formed between an alkyl group and an oxygen atom wherein the oxygen atom is used to attach the alkoxy group to a parent molecule. Examples of alkoxy groups include, but are not limited to, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups. As used herein, the terms "halo" and "halogen," as used herein, refer to an atom selected from fluorine, chlorine, bromine and iodine.

As used herein, the terms "aryl" and "aromatic," as used herein, refer to a mono- or polycyclic carbocyclic ring system radicals having one or more aromatic rings. Examples of aryl groups include, but are not limited to, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, the terms "aralkyl" and "arylalkyl," as used herein, refer to a radical formed between an alkyl group and an aryl group wherein the alkyl group is used to attach the aralkyl group to a parent molecule. Examples include, but are not limited to, benzyl, phenethyl and the like. Aralkyl groups as used herein may optionally include further substituent groups attached to the alkyl, the aryl or both groups that form the radical group.

As used herein, the term "heterocyclic radical" as used herein, refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic group typically includes at least one atom selected from sulfur, nitrogen or oxygen. Examples of heterocyclic groups include, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substituent groups. As used herein, the terms "heteroaryl," and "heteroaromatic," as used herein, refer to a radical comprising a mono- or polycyclic aromatic ring, ring system or fused ring system wherein at least one of the rings is aromatic and includes one or more heteroatom. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. Heteroaryl radicals can be attached to a parent molecule directly or through a linking moiety such as an aliphatic group or hetero atom. Heteroaryl groups as used herein may optionally include further substituent groups.

As used herein, the term "heteroarylalkyl," as used herein, refers to a heteroaryl group as previously defined having an alky radical that can attach the heteroarylalkyl group to a parent molecule. Examples include, but are not limited to, pyridinylmethyl, pyrimidinylethyl, napthyridinylpropyl and the like. Heteroarylalkyl groups as used herein may optionally include further substituent groups on one or both of the heteroaryl or alkyl portions.

As used herein, the term "mono or poly cyclic structure" as used in the present invention includes all ring systems that are single or polycyclic having rings that are fused or linked and is meant to be inclusive of single and mixed ring systems individually selected from aliphatic, alicyclic, aryl, heteroaryl, aralkyl, arylalkyl, heterocyclic, heteroaryl, heteroaromatic, heteroarylalkyl. Such mono and poly cyclic structures can contain rings that are uniform or have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two =O groups attached to one of the rings. In another aspect, mono or poly cyclic structures can be attached to a parent molecule directly through a ring atom, through a substituent group or a bifunctional linking moiety.

As used herein, the term "acyl," as used herein, refers to a radical formed by removal of a hydroxyl group from an organic acid and has the general formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, the term "hydrocarbyl" includes groups comprising C, O and H. Included are straight, branched and cyclic groups having any degree of saturation. Such hydrocarbyl groups can include one or more heteroatoms selected from N, O and S and can be further mono or poly substituted with one or more substituent groups.

As used herein, the terms "substituent" and "substituent group," as used herein, include groups that are typically added to other groups or parent compounds to enhance desired properties or give desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound. Such groups include without limitation, halogen, hydroxyl, alkyl, alkenyl, alkynyl, acyl (—C(O)Raa), carboxyl (—C(O)O—Raa), aliphatic groups, alicyclic groups, alkoxy, substituted oxo (—O—Raa), aryl, aralkyl, heterocyclic, heteroaryl, heteroarylalkyl, amino (—NRbbRcc), imino (=NRbb), amido (—C(O)N—RbbRcc or —N(Rbb)C(O)Raa), azido (—N3), nitro (—NO2), cyano (—CN), carbamido (—OC(O)NRbbRcc or —N(Rbb)C(O)ORaa), ureido (—N(Rbb)C(O)NRbbRcc), thioureido (—N(Rbb)C(S)NRbbRcc), guanidinyl (—N(Rbb)C(=NRbb)NRbbRcc), amidinyl (—C(=NRbb)-NRbbRcc or —N(Rbb)C(NRbb)Raa), thiol (—SRbb), sulfinyl (—S(O)Rbb), sulfonyl (—S(O)2Rbb), sulfonamidyl (—S(O)2NRbbRcc or —N(Rbb)S(O)2Rbb) and conjugate groups. Wherein each Raa, Rbb and Rcc is, independently, H, an optionally linked chemical functional group or a further substituent group with a preferred list including without limitation H, alkyl, alkenyl, alkynyl, aliphatic, alkoxy, acyl, aryl, aralkyl, heteroaryl, alicyclic, heterocyclic and heteroarylalkyl.

Oligomeric Compounds

Antisense compounds and antidote compounds are oligomeric compounds. In certain embodiments, it is desirable to chemically modify oligomeric compounds, including antisense compounds and/or antidote oligomeric compounds, compared to naturally occurring oligomers, such as DNA or RNA. Certain such modifications alter the activity of the oligomeric compound. Certain such chemical modifications can alter activity by, for example: increasing affinity of an antisense compound for its target nucleic acid or an antidote for its antisense compound, increasing its resistance to one or more nucleases, and/or altering the pharmacokinetics or tissue distribution of the oligomeric compound. In certain instances, the use of chemistries that increase the affinity of an oligomeric compound for its target can allow for the use of shorter oligomeric compounds.

Certain Monomers

In certain embodiment, oligomeric compounds comprise one or more modified monomer. In certain such embodiments, oligomeric compounds comprise one or more high affinity monomer. In certain embodiments, such high-affinity monomer is selected from monomers (e.g., nucleosides and nucleotides) comprising 2'-modified sugars, including, but not limited to: BNA's and monomers (e.g., nucleosides and nucleotides) with 2'-substituents such as allyl, amino, azido, thio, O-allyl, O—C1-C10 alkyl, —OCF3, O—(CH2)2-O—CH3, 2'-O(CH2)2SCH3, O—(CH2)2-O—N(Rm)(Rn), or O—CH2-C(=O)—N(Rm)(Rn), where each Rm and Rn is, independently, H or substituted or unsubstituted C1-C10 alkyl.

In certain embodiments, the oligomeric compounds including, but no limited to antidote and antisense oligomeric compounds of the present invention, comprise one or more high affinity monomers provided that the oligomeric compound does not comprise a nucleotide comprising a 2'-O(CH2)nH, wherein n is one to six.

In certain embodiments, the oligomeric compounds including, but no limited to antidote and antisense oligomeric compounds, comprise one or more high affinity monomer provided that the oligomeric compound does not comprise a nucleotide comprising a 2'-OCH3 or a 2'-O(CH2)2OCH3.

In certain embodiments, the oligomeric compounds including, but no limited to antidote and antisense oligomeric compounds, comprise one or more high affinity monomer provided that the oligomeric compound does not comprise a α-L-Methyleneoxy (4'-CH2-O-2') BNA.

In certain embodiments, the oligomeric compounds including, but no limited to antidote and antisense oligomeric compounds, comprise one or more high affinity monomer provided that the oligomeric compound does not comprise a β-D-Methyleneoxy (4'-CH2-O-2') BNA.

In certain embodiments, the oligomeric compounds including, but no limited to antidote and antisense oligomeric compounds, comprise one or more high affinity monomer provided that the oligomeric compound does not comprise a α-L-Methyleneoxy (4'-CH2-O-2') BNA or β-D-Methyleneoxy (4'-CH2-O-2') BNA.

Certain Nucleobases

The naturally occurring base portion of a nucleoside is typically a heterocyclic base. The two most common classes of such heterocyclic bases are the purines and the pyrimidines. For those nucleosides that include a pentofuranosyl sugar, a phosphate group can be linked to the 2', 3' or 5' hydroxyl moiety of the sugar. In forming oligonucleotides, those phosphate groups covalently link adjacent nucleosides to one another to form a linear polymeric compound. Within oligonucleotides, the phosphate groups are commonly referred to as forming the internucleoside backbone of the oligonucleotide. The naturally occurring linkage or backbone of RNA and of DNA is a 3' to 5' phosphodiester linkage.

In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable with the compounds described herein. In certain embodiments, a modified nucleobase is a nucleobase that is fairly similar in structure to the parent nucleobase, such as for example a 7-deaza purine, a 5-methyl cytosine, or a G-clamp. In certain embodiments, nucleobase mimetic include more complicated structures, such as for example a tricyclic phenoxazine nucleobase mimetic. Methods for preparation of the above noted modified nucleobases are well known to those skilled in the art.

Certain Sugars

Oligomeric compounds provided herein may comprise one or more monomer, including a nucleoside or nucleotide, having a modified sugar moiety. For example, the furanosyl sugar ring of a nucleoside can be modified in a number of ways including, but not limited to, addition of a substituent group, bridging of two non-geminal ring atoms to form a bicyclic nucleic acid (BNA). In certain embodiments, oligomeric compounds comprise one or more monomers that is a BNA. In certain such embodiments, BNA s include, but are not limited to, (A) α-L-Methyleneoxy (4'-CH2-O-2') BNA, (B) β-D-Methyleneoxy (4'-CH2-O-2') BNA, (C) Ethyleneoxy (4'-(CH2)2-O-2') BNA, (D) Aminooxy (4'-CH2-O—N(R)-2') BNA and (E) Oxyamino (4'-CH2-N(R)—O-2') BNA, as depicted below:

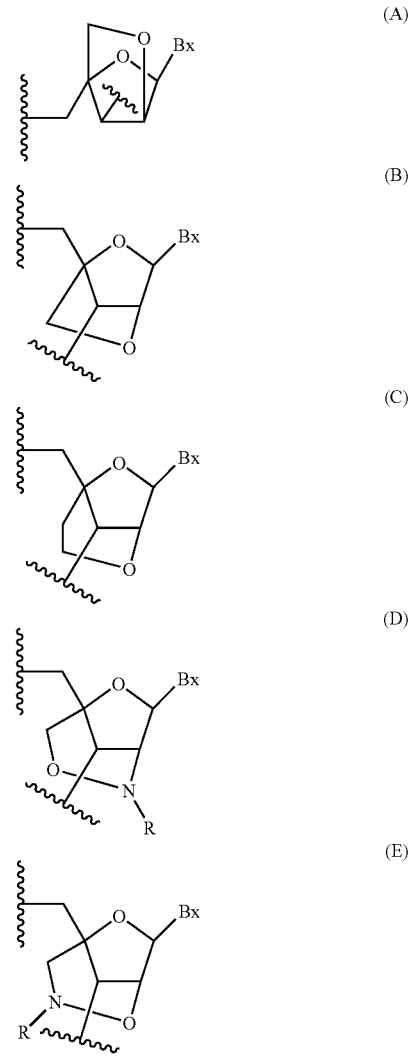

In certain embodiments, BNA compounds include, but are not limited to, compounds having at least one bridge between the 4' and the 2' position of the sugar wherein each of the bridges independently comprises 1 or from 2 to 4 linked groups independently selected from —[C(R1)(R2)]n-, —C(R1)=C(R2)-, —C(R1)=N—, —C(=NR1)-, —C(=O)—, —C(=S)—, —O—, —Si(R1)2-, —S(=O)x- and —N(R1)-;

wherein:
x is 0, 1, or 2;
n is 1, 2, 3, or 4;
each R1 and R2 is, independently, H, a protecting group, hydroxyl, C1-C12 alkyl, substituted C1-C12 alkyl, C2-C12 alkenyl, substituted C2-C12 alkenyl, C2-C12 alkynyl, substituted C2-C12 alkynyl, C5-C20 aryl, substituted C5-C20 aryl, heterocycle radical, substituted heterocycle radical, heteroaryl, substituted heteroaryl, C5-C7 alicyclic radical, substituted C5-C7 alicyclic radical, halogen, OJ1, NJ1J2, SJ1, N3, COOJ1, acyl (C(=O)—H), substituted acyl, CN, sulfonyl (S(=O)2-J1), or sulfoxyl (S(=O)-J1); and each J1 and J2 is, independently, H, C1-C12 alkyl, substituted C1-C12 alkyl, C2-C12 alkenyl, substituted C2-C12 alkenyl, C2-C12 alkynyl, substituted C2-C12 alkynyl, C5-C20 aryl, substituted C5-C20 aryl, acyl (C(=O)—H), substituted acyl, a heterocycle radical, a substituted heterocycle radical, C1-C12 aminoalkyl, substituted C1-C12 aminoalkyl or a protecting group.

In one embodiment, each of the bridges of the BNA compounds is, independently, —[C(R1)(R2)]n-, —[C(R1)(R2)]n-O—, —C(R1R2)-N(R1)-O— or —C(R1R2)-O—N(R1)-. In another embodiment, each of said bridges is, independently, 4'-CH2-2',4'-(CH2)2-2',4'-(CH2)3-2',4'-CH2-O-2',4'-(CH2)2-O-2',4'-CH2-O—N(R1)-2' and 4'-CH2-N(R1)-O-2' wherein each R1 is, independently, H, a protecting group or C1-C12 alkyl.

Certain BNA's have been prepared and disclosed in the patent literature as well as in scientific literature (Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; WO 94/14226; WO 2005/021570; Singh et al., J. Org. Chem., 1998, 63, 10035-10039; Examples of issued US patents and published applications that disclose BNA s include, for example, U.S. Pat. Nos. 7,053,207; 6,268,490; 6,770,748; 6,794,499; 7,034,133; and 6,525,191; and U.S. Pre-Grant Publication Nos. 2004-0171570; 2004-0219565; 2004-0014959; 2003-0207841; 2004-0143114; and 20030082807.

Also provided herein are BNAs in which the 2'-hydroxyl group of the ribosyl sugar ring is linked to the 4' carbon atom of the sugar ring thereby forming a methyleneoxy (4'-CH2-O-2') linkage to form the bicyclic sugar moiety (reviewed in Elayadi et al., Curr. Opinion Invens. Drugs, 2001, 2, 558-561; Braasch et al., Chem. Biol., 2001, 8 1-7; and Orum et al., Curr. Opinion Mol. Ther., 2001, 3, 239-243; see also U.S. Pat. Nos. 6,268,490 and 6,670,461). The linkage can be a methylene (—CH2-) group bridging the 2' oxygen atom and the 4' carbon atom, for which the term methyleneoxy (4'-CH2-O-2') BNA is used for the bicyclic moiety; in the case of an ethylene group in this position, the term ethyleneoxy (4'-CH2CH2-O-2') BNA is used (Singh et al., Chem. Commun., 1998, 4, 455-456: Morita et al., Bioorganic Medicinal Chemistry, 2003, 11, 2211-2226). Methyleneoxy (4'-CH2-O-2') BNA and other bicyclic sugar analogs display very high duplex thermal stabilities with complementary DNA and RNA (Tm=+3 to +10° C.), stability towards 3'-exonucleolytic degradation and good solubility properties. Potent and nontoxic antisense oligonucleotides comprising BNAs have been described (Wahlestedt et al., Proc. Natl. Acad. Sci. U.S.A., 2000, 97, 5633-5638).

An isomer of methyleneoxy (4'-CH2-O-2') BNA that has also been discussed is alpha-L-methyleneoxy (4'-CH2-O-2')

BNA which has been shown to have superior stability against a 3'-exonuclease. The alpha-L-methyleneoxy (4'-CH2-O-2') BNA's were incorporated into antisense gapmers and chimeras that showed potent antisense activity (Frieden et al., Nucleic Acids Research, 2003, 21, 6365-6372).

The synthesis and preparation of the methyleneoxy (4'-CH2-O-2') BNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). BNAs and preparation thereof are also described in WO 98/39352 and WO 99/14226.

Analogs of methyleneoxy (4'-CH2-O-2') BNA, phosphorothioate-methyleneoxy (4'-CH2-O-2') BNA and 2'-thio-BNAs, have also been prepared (Kumar et al., Bioorg. Med. Chem. Lett., 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., J. Org. Chem., 1998, 63, 10035-10039). In addition, 2'-Amino- and 2'-methylamino-BNA's have been prepared and the thermal stability of their duplexes with complementary RNA and DNA strands has been previously reported.

Modified sugar moieties are well known and can be used to alter, typically increase, the affinity of the antisense compound for its target and/or increase nuclease resistance. A representative list of preferred modified sugars includes but is not limited to bicyclic modified sugars (BNA's), including methyleneoxy (4'-CH2-O-2') BNA and ethyleneoxy (4'-(CH2)2-O-2' bridge) BNA; substituted sugars, especially 2'-substituted sugars having a 2'-F, 2'-OCH3 or a 2'-O(CH2)2-OCH3 substituent group; and 4'-thio modified sugars. Sugars can also be replaced with sugar mimetic groups among others. Methods for the preparations of modified sugars are well known to those skilled in the art. Some representative patents and publications that teach the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; 6,531,584; and 6,600,032; and WO 2005/121371.

In certain embodiments, BNA's include bicyclic nucleoside having the formula:

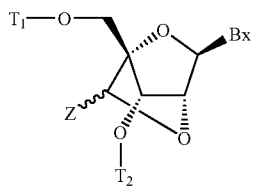

wherein:
Bx is a heterocyclic base moiety;
T1 is H or a hydroxyl protecting group;
T2 is H, a hydroxyl protecting group or a reactive phosphorus group;
Z is C1-C6 alkyl, C2-C6 alkenyl, C2-C6 alkynyl, substituted C1-C6 alkyl, substituted C2-C6 alkenyl, substituted C2-C6 alkynyl, acyl, substituted acyl, or substituted amide.

In one embodiment, each of the substituted groups, is, independently, mono or poly substituted with optionally protected substituent groups independently selected from halogen, oxo, hydroxyl, OJ1, NJ1J2, SJ1, N3, OC(=X)J1, OC(=X)NJ1J2, NJ3C(=X)NJ1J2 and CN, wherein each J1, J2 and J3 is, independently, H or C1-C6 alkyl, and X is O, S or NJ1.

In certain such embodiments, each of the substituted groups, is, independently, mono or poly substituted with substituent groups independently selected from halogen, oxo, hydroxyl, OJ1, NJ1J2, SJ1, N3, OC(=X)J1, and NJ3C(=X)NJ1J2, wherein each J1, J2 and J3 is, independently, H, C1-C6 alkyl, or substituted C1-C6 alkyl and X is O or NJ1.

In certain embodiments, the Z group is C1-C6 alkyl substituted with one or more Xx, wherein each Xx is independently OJ1, NJ1J2, SJ1, N3, OC(=X)J1, OC(=X)NJ1J2, NJ3C(=X)NJ1J2 or CN; wherein each J1, J2 and J3 is, independently, H or C1-C6 alkyl, and X is O, S or NJ1. In another embodiment, the Z group is C1-C6 alkyl substituted with one or more Xx, wherein each Xx is independently halo (e.g., fluoro), hydroxyl, alkoxy (e.g., CH3O—), substituted alkoxy or azido.

In certain embodiments, the Z group is —CH2Xx, wherein Xx is OJ1, NJ1J2, SJ1, N3, OC(=X)J1, OC(=X)NJ1J2, NJ3C(=X)NJ1J2 or CN; wherein each J1, J2 and J3 is, independently, H or C1-C6 alkyl, and X is O, S or NJ1. In another embodiment, the Z group is —CH2Xx, wherein Xx is halo (e.g., fluoro), hydroxyl, alkoxy (e.g., CH3O—) or azido.

In certain such embodiments, the Z group is in the (R)-configuration:

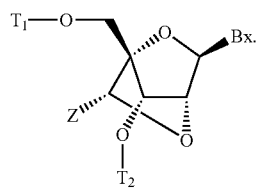

In certain such embodiments, the Z group is in the (S)-configuration:

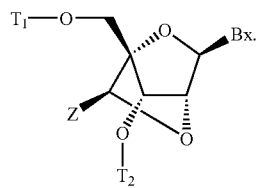

In certain embodiments, each T1 and T2 is a hydroxyl protecting group. A preferred list of hydroxyl protecting groups includes benzyl, benzoyl, 2,6-dichlorobenzyl, t-butyldimethylsilyl, t-butyldiphenylsilyl, mesylate, tosylate, dimethoxytrityl (DMT), 9-phenylxanthine-9-yl (Pixyl) and 9-(p-methoxyphenyl)xanthine-9-yl (MOX). In certain embodiments, T1 is a hydroxyl protecting group selected from acetyl, benzyl, t-butyldimethylsilyl, t-butyldiphenylsilyl and dimethoxytrityl wherein a more preferred hydroxyl protecting group is T1 is 4,4'-dimethoxytrityl.

In embodiments, T2 is a reactive phosphorus group wherein preferred reactive phosphorus groups include diisopropylcyanoethoxy phosphoramidite and H-phosphonate. In certain embodiments T1 is 4,4'-dimethoxytrityl and T2 is diisopropylcyanoethoxy phosphoramidite.

In certain embodiments, oligomeric compounds have at least one monomer of the formula:

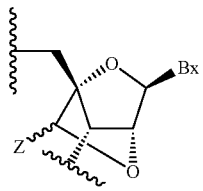

or of the formula:

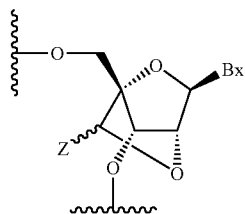

or of the formula:

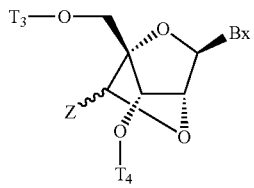

wherein
Bx is a heterocyclic base moiety;
T3 is H, a hydroxyl protecting group, a linked conjugate group or an internucleoside linking group attached to a nucleoside, a nucleotide, an oligonucleoside, an oligonucleotide, a monomeric subunit or an oligomeric compound;
T4 is H, a hydroxyl protecting group, a linked conjugate group or an internucleoside linking group attached to a nucleoside, a nucleotide, an oligonucleoside, an oligonucleotide, a monomeric subunit or an oligomeric compound;
wherein at least one of T3 and T4 is an internucleoside linking group attached to a nucleoside, a nucleotide, an oligonucleoside, an oligonucleotide, a monomeric subunit or an oligomeric compound; and
Z is C1-C6 alkyl, C2-C6 alkenyl, C2-C6 alkynyl, substituted C1-C6 alkyl, substituted C2-C6 alkenyl, substituted C2-C6 alkynyl, acyl, substituted acyl, or substituted amide.

In one embodiment, each of the substituted groups, is, independently, mono or poly substituted with optionally protected substituent groups independently selected from halogen, oxo, hydroxyl, OJ1, NJ1J2, SJ1, N3, OC(=X)J1, OC(=X)NJ1J2, NJ3C(=X)NJ1J2 and CN, wherein each J1, J2 and J3 is, independently, H or C1-C6 alkyl, and X is O, S or NJ1.

In one embodiment, each of the substituted groups, is, independently, mono or poly substituted with substituent groups independently selected from halogen, oxo, hydroxyl, OJ1, NJ1J2, SJ1, N3, OC(=X)J1, and NJ3C(=X)NJ1J2, wherein each J1, J2 and J3 is, independently, H or C1-C6 alkyl, and X is O or NJ1.

In certain such embodiments, at least one Z is C1-C6 alkyl or substituted C1-C6 alkyl. In certain embodiments, each Z is, independently, C1-C6 alkyl or substituted C1-C6 alkyl. In certain embodiments, at least one Z is C1-C6 alkyl. In certain embodiments, each Z is, independently, C1-C6 alkyl. In certain embodiments, at least one Z is methyl. In certain embodiments, each Z is methyl. In certain embodiments, at least one Z is ethyl. In certain embodiments, each Z is ethyl. In certain embodiments, at least one Z is substituted C1-C6 alkyl. In certain embodiments, each Z is, independently, substituted C1-C6 alkyl. In certain embodiments, at least one Z is substituted methyl. In certain embodiments, each Z is substituted methyl. In certain embodiments, at least one Z is substituted ethyl. In certain embodiments, each Z is substituted ethyl.

In certain embodiments, at least one substituent group is C1-C6 alkoxy (e.g., at least one Z is C1-C6 alkyl substituted with one or more C1-C6 alkoxy). In another embodiment, each substituent group is, independently, C1-C6 alkoxy (e.g., each Z is, independently, C1-C6 alkyl substituted with one or more C1-C6 alkoxy).

In certain embodiments, at least one C1-C6 alkoxy substituent group is CH3O— (e.g., at least one Z is CH3OCH2-). In another embodiment, each C1-C6 alkoxy substituent group is CH3O— (e.g., each Z is CH3OCH2-).

In certain embodiments, at least one substituent group is halogen (e.g., at least one Z is C1-C6 alkyl substituted with one or more halogen). In certain embodiments, each substituent group is, independently, halogen (e.g., each Z is, independently, C1-C6 alkyl substituted with one or more halogen). In certain embodiments, at least one halogen substituent group is fluoro (e.g., at least one Z is CH2FCH2-, CHF2CH2- or CF3CH2-). In certain embodiments, each halo substituent group is fluoro (e.g., each Z is, independently, CH2FCH2-, CHF2CH2- or CF3CH2-).

In certain embodiments, at least one substituent group is hydroxyl (e.g., at least one Z is C1-C6 alkyl substituted with one or more hydroxyl). In certain embodiments, each substituent group is, independently, hydroxyl (e.g., each Z is, independently, C1-C6 alkyl substituted with one or more hydroxyl). In certain embodiments, at least one Z is HOCH2-. In another embodiment, each Z is HOCH2-.

In certain embodiments, at least one Z is CH3-, CH3CH2-, CH2OCH3-, CH2F— or HOCH2-. In certain embodiments, each Z is, independently, CH3-, CH3CH2-, CH2OCH3-, CH2F— or HOCH2-.

In certain embodiments, at least one Z group is C1-C6 alkyl substituted with one or more Xx, wherein each Xx is, independently, OJ1, NJ1J2, SJ1, N3, OC(=X)J1, OC(=X)NJ1J2, NJ3C(=X)NJ1J2 or CN; wherein each J1, J2 and J3 is, independently, H or C1-C6 alkyl, and X is O, S or NJ1. In another embodiment, at least one Z group is C1-C6 alkyl substituted with one or more Xx, wherein each Xx is, independently, halo (e.g., fluoro), hydroxyl, alkoxy (e.g., CH3O—) or azido.

In certain embodiments, each Z group is, independently, C1-C6 alkyl substituted with one or more Xx, wherein each Xx is independently OJ1, NJ1J2, SJ1, N3, OC(=X)J1, OC(=X)NJ1J2, NJ3C(=X)NJ1J2 or CN; wherein each J1, J2 and J3 is, independently, H or C1-C6 alkyl, and X is O, S or NJ1. In another embodiment, each Z group is, independently, C1-C6 alkyl substituted with one or more Xx, wherein each Xx is independently halo (e.g., fluoro), hydroxyl, alkoxy (e.g., CH3O—) or azido.

In certain embodiments, at least one Z group is —CH2Xx, wherein Xx is OJ1, NJ1J2, SJ1, N3, OC(=X)J1, OC(=X)NJ1J2, NJ3C(=X)NJ1J2 or CN; wherein each J1, J2 and J3 is, independently, H or C1-C6 alkyl, and X is O, S or NJ1 In certain embodiments, at least one Z group is —CH2Xx, wherein Xx is halo (e.g., fluoro), hydroxyl, alkoxy (e.g., CH3O—) or azido.

In certain embodiments, each Z group is, independently, —CH2Xx, wherein each Xx is, independently, OJ1, NJ1J2, SJ1, N3, OC(=X)J1, OC(=X)NJ1J2, NJ3C(=X)NJ1J2 or CN; wherein each J1, J2 and J3 is, independently, H or C1-C6 alkyl, and X is O, S or NJ1. In another embodiment, each Z group is, independently, —CH2Xx, wherein each Xx is, independently, halo (e.g., fluoro), hydroxyl, alkoxy (e.g., CH3O—) or azido.

In certain embodiments, at least one Z is CH3-. In another embodiment, each Z is, CH3-.

In certain embodiments, the Z group of at least one monomer is in the (R)— configuration represented by the formula:

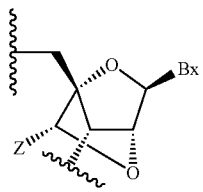

or the formula:

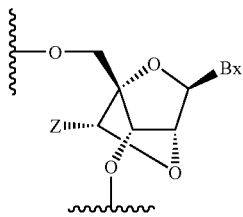

or the formula:

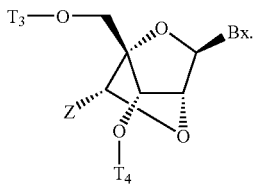

In certain embodiments, the Z group of each monomer of the formula is in the (R)—configuration.

In certain embodiments, the Z group of at least one monomer is in the (S)— configuration represented by the formula:

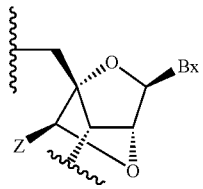

or the formula:

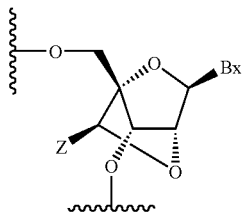

or the formula:

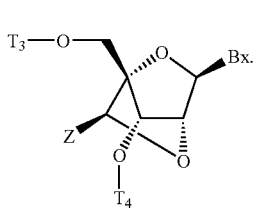

In certain embodiments, the Z group of each monomer of the formula is in the (S)— configuration.

In certain embodiments, T3 is H or a hydroxyl protecting group. In certain embodiments, T4 is H or a hydroxyl protecting group. In a further embodiment T3 is an internucleoside linking group attached to a nucleoside, a nucleotide or a monomeric subunit. In certain embodiments, T4 is an internucleoside linking group attached to a nucleoside, a nucleotide or a monomeric subunit. In certain embodiments, T3 is an internucleoside linking group attached to an oligonucleoside or an oligonucleotide. In certain embodiments, T4 is an internucleoside linking group attached to an oligonucleoside or an oligonucleotide. In certain embodiments, T3 is an internucleoside linking group attached to an oligomeric compound. In certain embodiments, T4 is an internucleoside linking group attached to an oligomeric compound. In certain embodiments, at least one of T3 and T4 comprises an internucleoside linking group selected from phosphodiester or phosphorothioate.

In certain embodiments, oligomeric compounds have at least one region of at least two contiguous monomers of the formula:

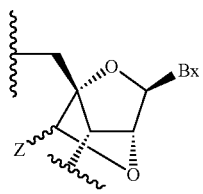

or of the formula:

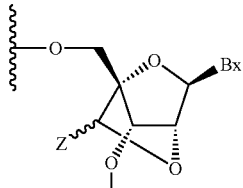

or of the formula:
to

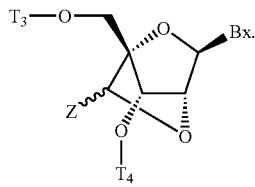

In certain embodiments, the oligomeric compound comprises at least two regions of at least two contiguous monomers of the above formula. In certain embodiments, the oligomeric compound comprises a gapped oligomeric compound. In certain embodiments, the oligomeric compound comprises at least one region of from about 8 to about 14 contiguous β-D-2'-deoxyribofuranosyl nucleosides. In certain embodiments, the oligomeric compound comprises at least one region of from about 9 to about 12 contiguous β-D-2'-deoxyribofuranosyl nucleosides.

In certain embodiments, monomers include sugar mimetics. In certain such embodiments, a mimetic is used in place of the sugar or sugar-internucleoside linkage combination, and the nucleobase is maintained for hybridization to a selected target. Representative examples of a sugar mimetics include, but are not limited to, cyclohexenyl or morpholino. Representative examples of a mimetic for a sugar-internucleoside linkage combination include, but are not limited to, peptide nucleic acids (PNA) and morpholino groups linked by uncharged achiral linkages. In some instances a mimetic is used in place of the nucleobase. Representative nucleobase mimetics are well known in the art and include, but are not limited to, tricyclic phenoxazine analogs and universal bases (Berger et al., Nuc Acid Res. 2000, 28:2911-14, incorporated herein by reference). Methods of synthesis of sugar, nucleoside and nucleobase mimetics are well known to those skilled in the art.

Monomeric Linkages

Described herein are linking groups that link monomers (including, but not limited to, modified and unmodified nucleosides and nucleotides) together, thereby forming an oligomeric compound. The two main classes of linking groups are defined by the presence or absence of a phosphorus atom. Representative phosphorus containing linkages include, but are not limited to, phosphodiesters (P=O), phosphotriesters, methylphosphonates, phosphoramidate, and phosphorothioates (P=S). Representative non-phosphorus containing linking groups include, but are not limited to, methylenemethylimino (—CH2-N(CH3)-O—CH2-), thiodiester (—O—C(O)—S—), thionocarbamate (—O—C(O)(NH)—S—); siloxane (—O—Si(H)2-O—); and N,N'-dimethylhydrazine (—CH2-N(CH3)-N(CH3)-). Oligomeric compounds having non-phosphorus linking groups are referred to as oligonucleosides. Modified linkages, compared to natural phosphodiester linkages, can be used to alter, typically increase, nuclease resistance of the oligomeric compound. In certain embodiments, linkages having a chiral atom can be prepared a racemic mixtures, as separate enantiomers. Representative chiral linkages include, but are not limited to, alkylphosphonates and phosphorothioates. Methods of preparation of phosphorous-containing and non-phosphorous-containing linkages are well known to those skilled in the art.

The oligomeric compounds described herein contain one or more asymmetric centers and thus give rise to enantiomers, diastereomers, and other stereoisomeric configurations that may be defined, in terms of absolute stereochemistry, as (R) or (S), such as for sugar anomers, or as (D) or (L) such as for amino acids et al. Included in the antisense compounds provided herein are all such possible isomers, as well as their racemic and optically pure forms.

Oligomeric Compounds

In certain embodiments, provided herein are oligomeric compounds having reactive phosphorus groups useful for forming linkages including for example phosphodiester and phosphorothioate internucleoside linkages. Methods of preparation and/or purification of precursors or oligomeric compounds are not a limitation of the compositions or methods provided herein. Methods for synthesis and purification of oligomeric compounds including DNA, RNA, oligonucleotides, oligonucleosides, and antisense compounds are well known to those skilled in the art.

Generally, oligomeric compounds comprise a plurality of monomeric subunits linked together by linking groups. Non-limiting examples of oligomeric compounds include primers, probes, antisense compounds, antisense oligonucleotides, external guide sequence (EGS) oligonucleotides, alternate splicers, and siRNAs. As such, these compounds can be introduced in the form of single-stranded, double-stranded, circular, branched or hairpins and can contain structural elements such as internal or terminal bulges or loops. Oligomeric double-stranded compounds can be two strands hybridized to form double-stranded compounds or a single strand with sufficient self complementarity to allow for hybridization and formation of a fully or partially double-stranded compound.

In certain embodiments, the present invention provides chimeric oligomeric compounds. In certain such embodiments, chimeric oligomeric compounds are chimeric oligonucleotides. In certain such embodiments, the chimeric oligonucleotides comprise differently modified nucleotides. In certain embodiments, chimeric oligonucleotides are mixed-backbone antisense oligonucleotides.

In general a chimeric oligomeric compound will have modified nucleosides that can be in isolated positions or grouped together in regions that will define a particular motif. Any combination of modifications and/or mimetic groups can comprise a chimeric oligomeric compound as described herein.

In certain embodiments, chimeric oligomeric compounds typically comprise at least one region modified so as to confer increased resistance to nuclease degradation, increased cellular uptake, and/or increased binding affinity for the target nucleic acid. In certain embodiments, an additional region of the oligomeric compound may serve as a substrate for enzymes capable of cleaving RNA:DNA or RNA:RNA hybrids.

In certain embodiments, chimeric oligomeric compounds are gapmers. In certain such embodiments, a mixed-backbone oligomeric compound has one type of internucleotide linkages in one or both wings and a different type of internucleoside linkages in the gap. In certain such embodiments, the mixed-backbone oligonucleotide has phosphodiester linkages in the wings and phosphorothioate linkages in the gap. In certain embodiments in which the internucleoside linkages in a wing is different from the internucleoside linkages in the gap, the internucleoside linkage bridging that wing and the gap is the same as the internucleoside linkage in the wing. In certain embodiments in which the internucleoside linkages in a wing is different from the internucleoside linkages in the gap, the internucleoside linkage bridging that wing and the gap is the same as the internucleoside linkage in the gap.

In certain embodiments, the present invention provides oligomeric compounds, including antisense oligomeric compounds and antidote oligomeric compounds, of any of a variety of ranges of lengths. In certain embodiments, the invention provides oligomeric compounds consisting of X-Y linked oligonucleosides, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, the invention provides oligomeric compounds comprising: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-29, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked nucleosides.

Certain Conjugate Groups

In certain embodiments, oligomeric compounds are modified by covalent attachment of one or more conjugate groups. In general, conjugate groups modify one or more properties of the attached oligomeric compound including but not limited to pharmacodynamic, pharmacokinetic, binding, absorption, cellular distribution, cellular uptake, charge and clearance. Conjugate groups are routinely used in the chemical arts and are linked directly or via an optional linking moiety or linking group to a parent compound such as an oligomeric compound. A preferred list of conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

Preferred conjugate groups amenable to the present invention include lipid moieties such as a cholesterol moiety (Letsinger et al., Proc. Natl. Acad. Sci. USA, 1989, 86, 6553); cholic acid (Manoharan et al., Bioorg. Med. Chem. Lett., 1994, 4, 1053); a thioether, e.g., hexyl-S-tritylthiol (Manoharan et al., Ann. N.Y. Acad. Sci., 1992, 660, 306; Manoharan et al., Bioorg. Med. Chem. Let., 1993, 3, 2765); a thiocholesterol (Oberhauser et al., Nucl. Acids Res., 1992, 20, 533); an aliphatic chain, e.g., dodecandiol or undecyl residues (Saison-Behmoaras et al., EMBO J., 1991, 10, 111; Kabanov et al., FEBS Lett., 1990, 259, 327; Svinarchuk et al., Biochimie, 1993, 75, 49); a phospholipid, e.g., di-hexadecyl-rac-glycerol or triethylammonium-1,2-di-O-hexadecyl-rac-glycero-3-H-phosphonate (Manoharan et al., Tetrahedron Lett., 1995, 36, 3651; Shea et al., Nucl. Acids Res., 1990, 18, 3777); a polyamine or a polyethylene glycol chain (Manoharan et al., Nucleosides & Nucleotides, 1995, 14, 969); adamantane acetic acid (Manoharan et al., Tetrahedron Lett., 1995, 36, 3651); a palmityl moiety (Mishra et al., Biochim. Biophys. Acta, 1995, 1264, 229); or an octadecylamine or hexylamino-carbonyl-oxycholesterol moiety (Crooke et al., J. Pharmacol. Exp. Ther., 1996, 277, 923).

Linking groups or bifunctional linking moieties such as those known in the art are amenable to the compounds provided herein. Linking groups are useful for attachment of chemical functional groups, conjugate groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include, but are not limited to, substituted C1-C10 alkyl, substituted or unsubstituted C2-C10 alkenyl or substituted or unsubstituted C2-C10 alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Synthesis, Purification and Analysis

Oligomerization of modified and unmodified nucleosides and nucleotides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Oligomeric compounds provided herein can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The invention is not limited by the method of antisense compound synthesis.

Methods of purification and analysis of oligomeric compounds are known to those skilled in the art. Analysis methods include capillary electrophoresis (CE) and electrospray-mass spectroscopy. Such synthesis and analysis methods can be performed in multi-well plates. The method of the invention is not limited by the method of oligomer purification.

Compositions and Methods for Formulating Pharmaceutical Compositions

Oligomeric compounds may be admixed with pharmaceutically acceptable active and/or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

Oligomeric compounds, including antisense compounds and/or antidote compounds, can be utilized in pharmaceutical compositions by combining such oligomeric compounds with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound and/or antidote compound and a pharmaceutically acceptable diluent. In certain embodiments, the pharmaceutically acceptable diluent is PBS.

Pharmaceutical compositions comprising oligomeric compounds encompass any pharmaceutically acceptable salts, esters, or salts of such esters. In certain embodiments, pharmaceutical compositions comprising oligomeric compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active oligomeric compound.

Antisense

Antisense mechanisms are all those involving the hybridization of a compound with target nucleic acid, wherein the outcome or effect of the hybridization is either target degradation or target occupancy with concomitant stalling of the cellular machinery involving, for example, transcription or splicing.

For example, a type of antisense mechanism involving target degradation includes an RNase H. RNase H is a cellular endonuclease which cleaves the RNA strand of an RNA:DNA duplex. It is known in the art that single-stranded antisense compounds which are "DNA-like" elicit RNAse H activity in mammalian cells. Activation of RNase H, therefore, results in cleavage of the RNA target, thereby greatly enhancing the efficiency of DNA-like oligonucleotide-mediated inhibition of gene expression.

In certain embodiments, chemically-modified antisense compounds have a higher affinity for target RNAs than does non-modified DNA. In certain such embodiments, that higher affinity in turn provides increased potency allowing for the administration of lower doses of such compounds, reduced potential for toxicity and improvement in therapeutic index and decreased overall cost of therapy.

Antisense compounds are oligomeric compounds. Accordingly, in certain embodiments, antisense compounds comprise, for example and without limitation, any of the modifications and motifs described in the discussion above for oligomeric compounds. Antisense compounds may be single-stranded or double-stranded oligomeric compounds. In embodiments where an antisense compound is a double-stranded oligomeric compound, the two strands may have the same modifications and motifs or may have modifications and motifs that are different from one another. Certain antisense compounds and modifications and motifs useful for such compounds are known in the art.

Modulation of Target Expression

In certain embodiments, a target nucleic acid is a mRNA. In certain such embodiments, antisense compounds are designed to modulate that target mRNA or its expression. In certain embodiments, designing an antisense compound to a target nucleic acid molecule can be a multistep process. Typically the process begins with the identification of a target protein, the activity of which is to be modulated, and then identifying the nucleic acid the expression of which yields the target protein. In certain embodiments, designing of an antisense compound results in an antisense compound that is hybridizable to the targeted nucleic acid molecule. In certain embodiments, the antisense compound is an antisense oligonucleotide or antisense oligonucleoside. In certain embodiments, an antisense compound and a target nucleic acid are complementary to one another. In certain such embodiments, an antisense compound is perfectly complementary to a target nucleic acid. In certain embodiments, an antisense compound includes one mismatch. In certain embodiments, an antisense compound includes two mismatches. In certain embodiments, an antisense compound includes three or more mismatches.

Modulation of expression of a target nucleic acid can be achieved through alteration of any number of nucleic acid functions. In certain embodiments, the functions of RNA to be modulated include, but are not limited to, translocation functions, which include, but are not limited to, translocation of the RNA to a site of protein translation, translocation of the RNA to sites within the cell which are distant from the site of RNA synthesis, and translation of protein from the RNA. RNA processing functions that can be modulated include, but are not limited to, splicing of the RNA to yield one or more RNA species, capping of the RNA, 3' maturation of the RNA and catalytic activity or complex formation involving the RNA which may be engaged in or facilitated by the RNA. Modulation of expression can result in the increased level of one or more nucleic acid species or the decreased level of one or more nucleic acid species, either temporally or by net steady state level. Thus, in one embodiment modulation of expression can mean increase or decrease in target RNA or protein levels. In another embodiment modulation of expression can mean an increase or decrease of one or more RNA splice products, or a change in the ratio of two or more splice products.

Hybridization

In certain embodiments, antisense compounds specifically hybridize when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, "stringent hybridization conditions" or "stringent conditions" refers to conditions under which an antisense compound will hybridize to its target sequence, but to a minimal number of other sequences. Stringent conditions are sequence-dependent and will be different in different circumstances, and "stringent conditions" under which antisense compounds hybridize to a target sequence are determined by the nature and composition of the antisense compounds and the assays in which they are being investigated.

It is understood in the art that incorporation of nucleotide affinity modifications may allow for a greater number of mismatches compared to an unmodified compound. Similarly, certain oligonucleotide sequences may be more tolerant to mismatches than other oligonucleotide sequences. One of ordinary skill in the art is capable of determining an appropriate number of mismatches between oligonucleotides, or between an oligonucleotide and a target nucleic acid, such as by determining melting temperature (Tm). Tm or $\Delta$Tm can be calculated by techniques that are familiar to one of ordinary skill in the art. For example, techniques described in Freier et al. (Nucleic Acids Research, 1997, 25, 22: 4429-4443) allow one of ordinary skill in the art to evaluate nucleotide modifications for their ability to increase the melting temperature of an RNA:DNA duplex.

Antidote

In certain instances it is desirable to inhibit antisense activity. For example, in certain embodiments where the antisense target is an mRNA, it is may be desirable to inhibit antisense activity and thereby restore expression of a target protein. For example, certain antisense compounds have been used therapeutically. In certain such uses, antisense compounds are long-acting. In certain instances, such long acting antisense compounds are desirable, for their convenience. In such instances, though, it may also be desirable to have a means to reverse the antisense activity of an antisense compound. For example, a patient may respond poorly to treatment or receive too high a dose. In such an instance, an antidote to the antisense compound may be administered to at least partially reduce the antisense activity of the antisense compound. In certain embodiments, the long-lasting effect of antisense compounds makes waiting for that effect to slowly diminish through natural clearance an unattractive option.

By way of example, and without limiting the present invention, certain antisense compounds are useful for inhibiting blood clotting factors (e.g., Factor II (prothrombin), Factor VII, Factor IX, etc.). Certain such antisense compounds may be found, for example in Provisional U.S. Application 60/980,376, which is hereby incorporated by reference in its entirety. Such antisense compounds have therapeutic potential as anticoagulants. Long half-lives make such antisense compounds particularly attractive, however, if a patient receives too high a dose, has surgery (where anti-coagulation is undesirable) or otherwise desires a decrease in the anti-coagulant effect, an antidote to the antisense anti-coagulant compound may be administered. Such antidote compound will restore coagulation function more quickly than simply waiting for natural clearance of the antisense compound. This example is provided for illustrative purposes. Antisense compounds have been designed to a vast number of targets, including without limitation, a vast number of messenger RNA (mRNA) targets and pre-mRNA targets, as well as a vast number of non-coding RNA targets. Antidotes provided herein are suitable for any antisense compound, regardless of the target or mechanism of the antisense compound.

In certain embodiments, the invention provides antidote compounds to an antisense compound targeted to an mRNA. In certain such embodiments, the target mRNA encodes a protein involved in metabolism. In certain such embodiments, the target mRNA encodes a protein involved in cardiac function. In certain embodiments, the target mRNA encodes a protein involved in blood-clotting. Antisense compounds targeting any of a variety of target proteins are known in the art. See, for example: Provisional U.S. Application 60/980, 376; U.S. application Ser. No. 11/745,429, each of which is hereby incorporated by reference in its entirety. Target mRNAs that may be modulated with antisense and then with an antidote compound include, but are not limited to those encoding any of the following: prothrombin (Factor II), Factor VII, Factor IX, Factor XI, ApoB, SGLT2, PTEN, SOD1, Huntingtin, PTP1B, ICAM-1, CRP, GCGR, GCCR, Clusterin, Survivin, elf-4-e, Hsp27, VLA-4, PCSK-9, DGAT2, and IL-4$\alpha$.

In certain embodiments, the invention provides antidote compound to an antisense compound that modulates splicing of a pre-mRNA. Certain such antisense compounds may be found for example in U.S. Pat. Nos. 6,172,216; and 6,210, 892; in U.S. application Ser. Nos. 10/672,501; 11/339,785; and 10/416,214; and in International Application Nos.: WO 2007/002390; WO 2007/028065; WO 2007/047913; each of which is hereby incorporated by reference in its entirety.

In certain embodiments, the invention provides antidote compound to an antisense compound that modulates a microRNA. Certain such antisense compounds may be found for example in U.S. application Ser. No. 10/909,125; International Application Nos.: WO03/029459, which is hereby incorporated by reference in its entirety.

Antisense activity may rely on any of variety of different mechanisms to exert an effect. For example, a particular antisense compound may function through RNase H cleavage, through the RISC pathway, and/or by blocking translation or altering splicing by simply occupying a target RNA. Antidote compounds may be designed to any antisense compound, regardless of the mechanism(s) of action of the antisense compound. Likewise, the antidote itself may work through any mechanism(s). For example, in certain embodiments, hybridization of the antidote compound to the antisense compound results in cleavage of the antisense compound. In certain such embodiments, cleavage is affected by RNase H. In certain embodiments, hybridization of the antidote to the antisense compounds does not result in cleavage of the antisense compound, but nonetheless reduces antisense activity.

In certain embodiments, because the antidote compound is in competition with the antisense target for binding with the antisense compound, it is desirable to modify the antidote compound to increase its affinity for the antisense compound. In certain embodiments, one or more nucleoside of the antidote compound is modified. In certain such embodiments, such modification increases the affinity of the antidote compound for the antisense compound. Such modifications are known in the art and include, but are not limited to, BNA, including, but not limited to LNA, and ENA, 2' substitutions including, but not limited to 2' MOE, 2'-F, 2'-O-alkyl, including, but not limited to 2'-OMe. Such modifications may be used in any combination. In certain embodiments, an antidote is an oligomeric compound. Such antidotes may comprise any modification or motif, including, but not limited to those discussed above and in the references cited herein.

Antidote compounds are oligomeric compounds. Accordingly, in certain embodiments, antidote compounds comprise, for example and without limitation, any of the modifications and motifs described in the discussion above for oligomeric compounds. Antisense compounds may be single-stranded or double-stranded oligomeric compounds. In embodiments where an antisense compound is a double-stranded oligomeric compound, the two strands may have the same modifications and motifs or may have modifications and motifs that are different from one another. Certain antisense compounds and modifications and motifs useful for such compounds are known in the art. Such modifications and motifs may likewise be useful for antidote compounds.

In certain embodiments, motifs are designed with consideration given to both the antisense compound and the antidote. For example, certain antisense compounds are RNA-like (certain such compounds may rely on RISC and/or other RNases for their activity). In certain embodiments, an antidote for such a compound could comprise 4 or more contiguous DNA-like monomers. In certain embodiments, the resulting RNA/DNA duplex could activate RNase H, resulting in cleavage of the RNA-like antisense compound. In certain embodiments, antidote activity does not depend on enzymatic activity. In certain such embodiments, compounds designed without regard for enzymatic compatibility may incorporate modifications to improve other attributes. For example, certain motifs yield oligomeric compounds with high affinity for a target nucleic acid, but that are unable to elicit enzymatic cleavage of that target. Such motifs may be useful for antidote compounds in embodiments where cleavage of the antisense compound is not necessary.

In certain embodiments, an antisense compound and corresponding antidote compound are the same length. In certain embodiments, an antisense compound and corresponding antidote compound are different lengths.

Non-limiting examples of antisense/antidote pairs is provided in the following table:

| Antisense Compound | | Antidote Compound | |
|---|---|---|---|
| Length | Motif | Length | Motif |
| 20 | 5-10-5 MOE gapmer | 20 | 5-10-5 MOE gapmer |
| 20 | 5-10-5 MOE gapmer | 20 | Uniform MOE |
| 20 | 5-10-5 MOE gapmer | 20 | Uniform 2'-F |
| 20 | 5-10-5 MOE gapmer | 18 | Uniform BNA |
| 20 | 5-10-5 MOE gapmer | 20 | 5-10-5 LNA gapmer |
| 16 | 3-10-3 MOE gapmer | 16 | 3-10-3 MOE gapmer |
| 16 | 3-10-3 MOE gapmer | 14 | 2-10-2 LNA gapmer |
| 18 | 4-10-4 LNA gapmer | 18 | 4-10-4 LNA gapmer |
| 20 | Uniform 2'-F | 20 | Uniform 2'-F |
| 18 | 2-10-4-1 LNA-DNA-LNA-DNA | 20 | Uniform LNA |
| 14 | 2-10-2 BNA-RNA-BNA | 14 | Uniform BNA |

The above listed pairs of antisense and antidote compounds are only exemplary. One of skill in the art can select any length and motif for the sense and independently select any length and motif for the antidote compound. The antisense and antidote compounds may, likewise comprise modified internucleoside linkages in any combination.

Because the antidote compound is complementary to the antisense compound, it is at least partially identical to the antisense target nucleic acid (i.e., it is a sense strand). In certain embodiments, treatment with an antisense compound followed by an antidote compound could result in formation of a double-stranded duplex with antisense activity. For example, such a duplex could be an siRNA and activate the RISC pathway. In embodiments where a decrease of antisense activity is sought, such duplexes should be avoided. Thus, in certain embodiments, where the antisense compound comprises RNA-like nucleosides suitable for loading into RISC, the antidote compound should avoid modifications that will allow or facilitate such loading of the antisense compound into RISC.

In certain embodiments, an antisense compound and an antidote compound are administered to a patient. In certain such embodiments, pharmaceutical compositions comprising an antisense compound and those comprising an antidote compound comprise the same formulation. In certain embodiments, pharmaceutical compositions comprising an antisense compound and those comprising an antidote compound comprise different formulations. In certain embodiments an antisense compound and an antidote compound are administered by the same route. In certain embodiments an antisense compound and an antidote compound are administered by different routes. For example, in certain embodiments, an antisense compound is administered orally and an antidote compound is administered by injection. In certain embodiments, the dosages of the antisense compound and the antidote compound are the same. In certain embodiments, the dosages of the antisense compound and the antidote compound are different.

In certain embodiments, the toxicity profiles of the antisense compound and the antidote compound are similar. In certain embodiments, such toxicity profiles are different. For example, in certain embodiments, an antisense compound may be intended for chronic administration and the antidote compound is only intended for acute use as needed. In such embodiments, the tolerance for toxic side-effects of the antidote compound may be higher. Accordingly, modifications and motifs that may be too toxic for use in an antisense compound may be acceptable in an antidote compound. For example, in certain embodiments, oligomeric compounds comprising one or more LNA nucleoside have been shown to have high affinity for a target nucleic acid, but in certain embodiments have been shown to cause toxicity at relatively low concentrations. For certain antisense compounds, where chronic administration is intended, certain such compounds comprising LNA may not be suitable. However, in embodiments where an antidote compound is not intended for chronic administration, but rather for acute administration when antisense activity is problematic, such LNA modifications in an antidote compound may be acceptable. The increased affinity of LNA may improve the antidote effect and since the antidote is only administered for a short period of time, and possibly when the patient is in distress, the increased toxicity of LNA may be justified. Other high affinity, but potentially toxic modifications are known.

In certain embodiments, an antisense activity is counteracted by a non-oligomeric antidote. For example, in certain embodiments, when the target nucleic acid is a target mRNA encoding a protein it is desirable to reduce the antisense activity and to increase in the amount of the target protein (e.g., target protein amount has gone too low, or circumstances have changed resulting in the desire to restore target protein amount). In such embodiments, one may simply administer the target protein itself. Such administration will immediately reverse the antisense activity of target protein reduction. However, it may also be desirable to administer an oligomeric antidote compound according to the present invention. For example, the target protein may have a short half-life in the animal. Accordingly, to maintain the restored target protein concentration would require repeated administration of target protein until the antisense compound has cleared and normal protein expression is restored. In certain such embodiments, it is still desirable to administer an antidote compound to shorten the duration of the antisense activity. In certain embodiments an antidote compound is co-administered with a non-oligomeric antidote. In certain such embodiments, the non-oligomeric antidote is a target protein. In certain embodiments, the non-oligomeric antidote compound is a protein having similar physiological effect as a target protein or that stimulates expression of the target protein.

Research Tools

In certain instances, antisense compounds have been used as research tools. For example, researchers investigating the function of a particular gene product may design antisense compounds to reduce the amount of that gene product present in a cell or an animal and observe phenotypic changes in the cell or animal. In certain embodiments, the present invention provides methods for reducing the amount of a gene product in a cell or animal through antisense and then reducing that antisense activity, thereby restoring the inhibited gene product. In certain embodiments, investigators may use such techniques to characterize proteins or untranslated nucleic acids. In certain embodiments, investigators may vary the amount of time between antisense and antidote administration. In certain embodiments, such experiments are used to investigate kinetics and/or turnover of gene products and/or certain cellular functions.

Kits

In certain embodiments, the present invention provides kits comprising one or more antisense compound and one or more corresponding antidote compound. In certain embodiments, such kits are intended for therapeutic application. In certain embodiments, such kits are intended for research use.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

The nucleoside sequences set forth in the sequence listing and Examples, are independent of any modification to a sugar moiety, a monomeric linkage, or a nucleobase. As such, oligomeric compounds defined by a SEQ ID NO may comprise, independently, one or more modifications to a sugar moiety, an internucleoside linkage, or a nucleobase. Oligomeric compounds described by Isis Number (Isis NO.) indicate a combination of nucleobase sequence and one or more modifications to a sugar moiety, an internucleoside linkage, or a nucleobase, as indicated.

EXAMPLES

Example 1

Fas Antisense and Antidote Oligonucleotides

An antisense compound complementary to murine Fas and antidote compounds to that antisense compound were synthesized using an Applied Biosystems 380B automated DNA synthesizer (Applied Biosystems, Foster City, Calif.). Compound details are provided in Table 1, below.

TABLE 1

Fas antisense and antidotes

| ISIS # | Chemistry Motif | Sequence | Description | SEQ ID |
|---|---|---|---|---|
| 22023 | 5-10-5 MOE gap | TCCAGCACTTTCTTTTCCGG | Fas Antisense | 1 |
| 401770 | 5-10-5 MOE | CCGGAAAAGAAAGTGCTGGA | Antidote to 22023 | 2 |
| 401769 | Uniform MOE | CCGGAAAAGAAAGTGCTGGA | Antidote to 22026 | 2 |
| 29837 | 5-10-5 MOE | TCGATCTCCTTTTATGCCCG | Non-sense control | 3 |

Example 2

Fas Antisense/Antidote Treatment of Mice

Eight week old Balb/c mice (Charles River Laboratories (Willmington, Mass.)) were injected sub-cutaneously with 35 mg/kg of ISIS 22023 in a volume of 200 ml of saline or with 200 ml of saline (control mice) every other day for two injections.

One day after the second injection, the mice were divided into 3 groups: Group 1 received 35 mg/kg sub-cutaneous injections of ISIS 401770 (5-10-5 MOE gapmer antidote to ISIS 22023) once daily for two days; Group 2 received 35 mg/kg sub-cutaneous injections of ISIS 401769 (uniform MOE antidote to ISIS-22023) once daily for two days; and Group 3 received sub-cutaneous injections of saline once daily for two days. All injections were in a total volume of 200 µl of sterile saline. Animals were sacrificed and livers were collected at 2, 4, 7, 10, and 14 days after the first day of antidote treatment.

Example 3

Fas RNA

Total RNA was isolated from the livers using Rneasy mini kit (Quiagen). Fas RNA was assessed by quantitative real-time PCR, using standard techniques. Results are summarized in FIG. 1.

Treatment with antisense compound ISIS 22023 resulted in reduction of Fas mRNA. Subsequent treatment with antidote compound ISIS 401770 or ISIS 401769 reduced the antisense activity of ISIS 22023 (i.e., treatment with such compounds reduced the reduction of Fas mRNA).

Example 4

Kinetics and Specificity of Fas Antidotes

Part 1. To study the kinetic of the antidote activity, eight week old Balb/c mice were injected sub-cutaneously with 35 mg/kg of ISIS 22023 in a volume of 200 ml of saline or with 200 ml of saline (control mice) every other day for two injections.

Two days after the second injection, the mice were divided into 3 groups: Group 1 received a single 70 mg/kg sub-cutaneous injection of ISIS 401770 (5-10-5 MOE gapmer antidote to ISIS 22023); Group 2 received a single 70 mg/kg sub-cutaneous injection of ISIS 401769 (uniform MOE antidote to ISIS-22023); and Group 3 received a sub-cutaneous injection of saline. All injections were in a total volume of 200 µl of sterile saline. Animals were sacrificed and livers were collected at 6 hours, 12 hours and 1, 2, 6, and 14 days after antidote treatment.

Figure 2:
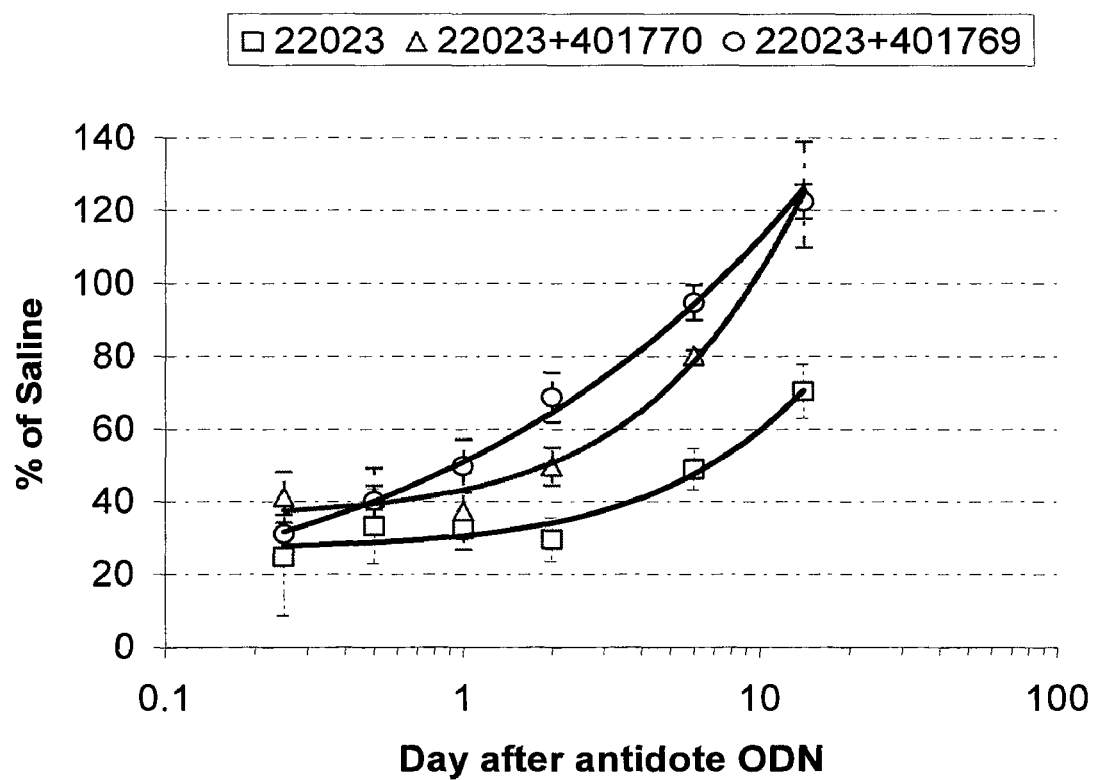
FIG. 2 shows Kinetics of Fas antisense and antidote activity as discussed in Example 4.

Livers were collected and total RNA was analyzed as described above (Example 3). Results are shown in FIG. 2.

To test the specificity of the antisense activity and the antidote activity, eight week old Balb/c mice were divided into 3 groups and injected sub-cutaneously using a first treatment (antisense stage) and a second treatment (antidote stage) as described above in part 1, using the compounds in Table 2, below:

TABLE 2

Compounds to test specificity of antisense/antidote activity

| Group | First (antisense) treatment | Second (antidote) treatment |
|---|---|---|
| 1 | 22023 (Fas antisense) | 29837 (non-sense control) |
| 2 | 29837 (non-sense control) | 401769 (antidote to 22023) |
| 3 | 29837 (non-sense control) | 401770 (antidote to 22023) |

Figure 3:
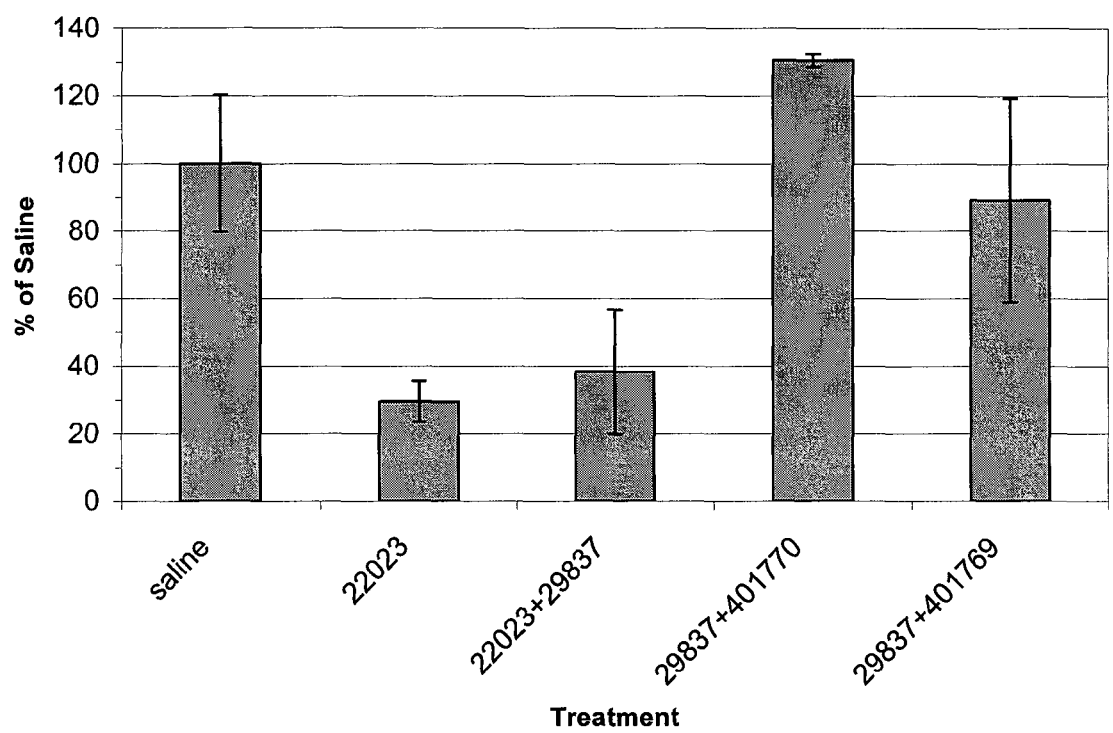
FIG. 3 shows Fas mRNA after treatment with antisense or mismatch antisense, followed by antidote or mismatch antidote as discussed in Example 4. The mismatch control oligonucleotide did not demonstrate antidote activity.

ISIS 29837 is a 5-10-5 MOE gapmer with the same base composition as ISIS 22023, but with the sequence scrambled, resulting 8 mismatches. Thus, it is not expected to be an effective antisense compound (groups 2 and 3) nor an effective antidote compound to 22023 (group 1). As shown in FIG. 3, the mismatch control oligonucleotide did not provide an antidote effect suggesting that the antidote effect is sequence specific.

Example 5

PTEN Antisense and Antidote Oligonucleotides

An antisense compound complementary to PTEN and antidote compounds to that antisense compound were synthesized using an Applied Biosystems 380B automated DNA synthesizer (Applied Biosystems, Foster City, Calif.). Compound details are provided in Table 3, below.

TABLE 3

Fas antisense and antidote compounds

| ISIS # | Chemistry Motif | Sequence | Description | SEQ ID |
|---|---|---|---|---|
| 116847 | 5-10-5 MOE gap | CTGCTAGCCTCTGGATTTGA | PTEN antisense | 4 |
| 126525 | Uniform MOE | TCAAATCCAGAGGCTAGCAG | Antidote to 116847 | 5 |
| 401769 | Uniform MOE | CCGGAAAGAAAGTGCTGGA | Non-sense control | 6 |

Example 6

PTEN Antisense/Antidote Treatment of Mice

Eight week old Balb/c mice (Charles River Laboratories (Willmingon, Mass.)) were injected sub-cutaneously with 35 mg/kg of ISIS 116847 (5-10-5 MOE gapmer PTEN antisense) in a volume of 200 ml of saline or with 200 ml of saline (control mice) every other day for two injections.

Two days after the second injection, the mice were divided into 3 groups: Group 1 received a single 70 mg/kg sub-cutaneous injection of ISIS 126525 (uniform MOE antidote to ISIS 116847); Group 2 received a single 70 mg/kg sub-cutaneous injection of ISIS 401769 (Uniform MOE antidote to Fas, used here as non-sense control); and Group 3 received a sub-cutaneous injection of saline. All injections were in a total volume of 200 µl of sterile saline. Samples were collected at 12 hours and 1, 2, 3, 7, and 14 days after antidote treatment.

Figure 4:
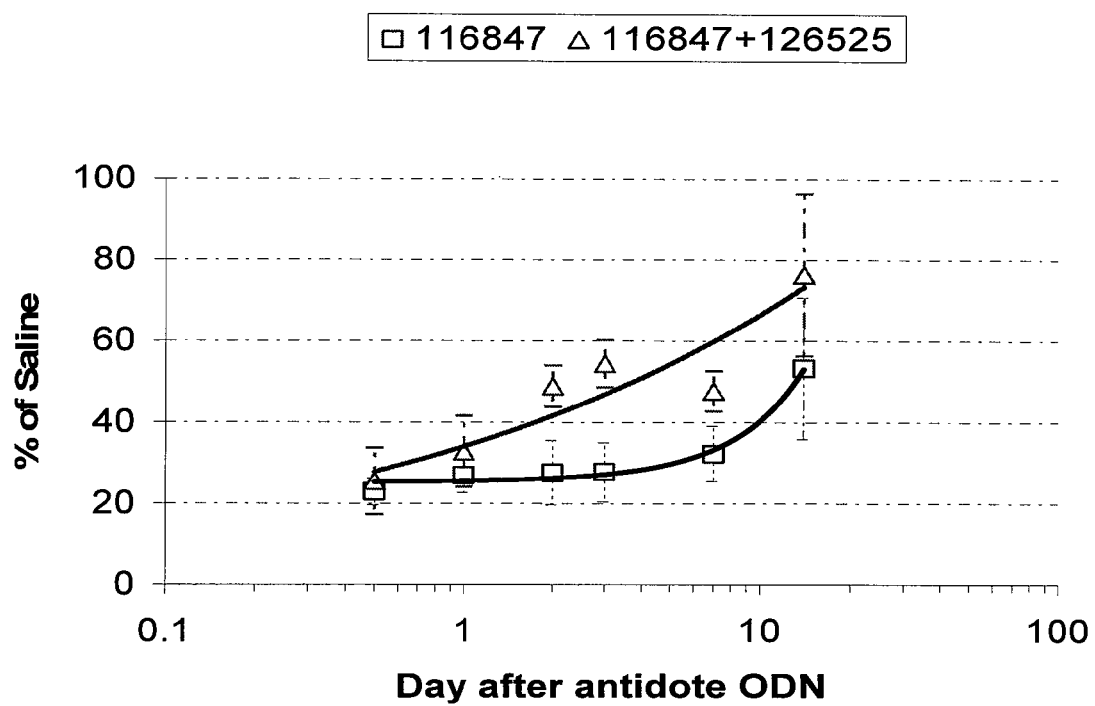
FIG. 4 shows PTEN mRNA levels following antisense treatment in mice followed by antidote treatment or by control injection as described in Example 6.
Figure 5:
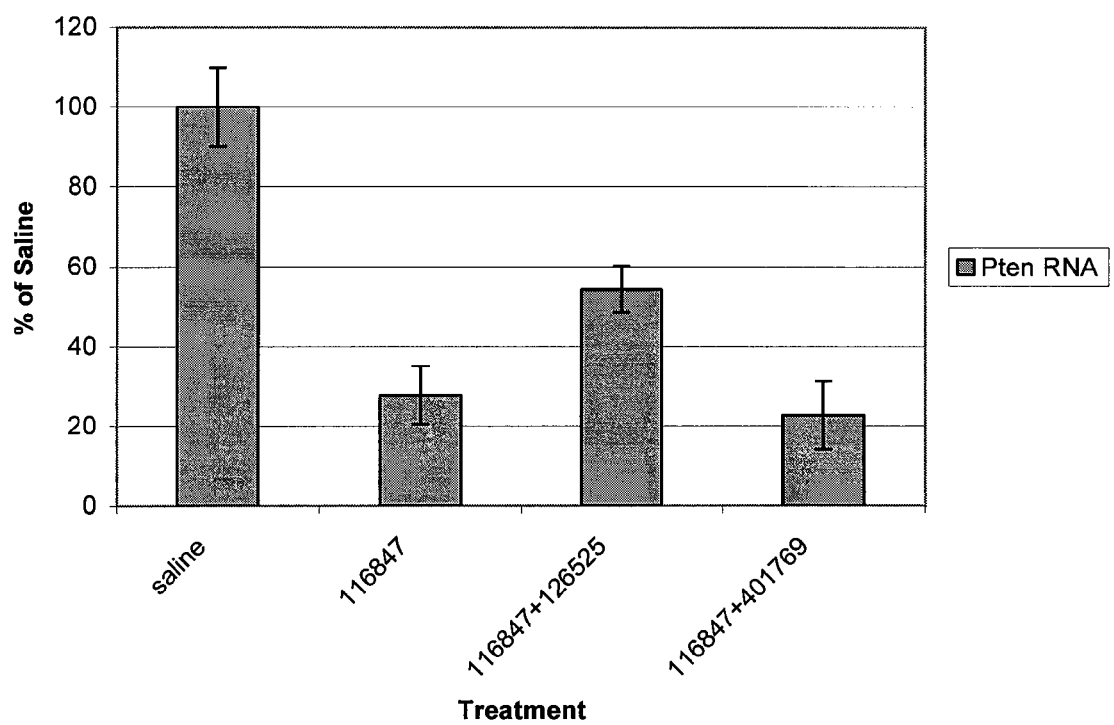
FIG. 5 shows PTEN mRNA levels in mice following treatments described in Example 6, demonstrating that (1) antisense compound ISIS 116847 reduced PTEN mRNA in mouse liver, (2) antidote compound ISIS 126525 partially restored PTEN mRNA by 3 days, and (3) ISIS 40169, which is used here as a non-sense control did not restore PTEN mRNA.

Samples were processed as described above in Example 3. Results are shown in FIGS. 4 and 5, below.

Example 7

Prothrombin Antisense and Antidote Oligonucleotides

An antisense compound complementary to prothrombin and antidote compounds to that antisense compound were synthesized using an Applied Biosystems 380B automated DNA synthesizer (Applied Biosystems, Foster City, Calif.). Compound details are provided in Table 4, below.

TABLE 4

Prothrombin antisense and antidote compounds

| ISIS # | Chemistry Motif | Sequence | Description | SEQ ID |
|---|---|---|---|---|
| 401025 | 5-10-5 MOE gap | ATTCCATAGTGTAGGCCTT | Prothrombin antisense | 7 |
| 405277 | 5-10-5 MOE gap | AAGGACCTACACTATGGAAT | Antidote to 401025 | 8 |
| 405278 | Uniform MOE | AAGGACCTACACTATGGAAT | Antidote to 401025 | 8 |

Example 8

Prothrombin Antisense/Antidote Treatment of Mice

Eight week old Balb/c mice (Charles River Laboratories (Willmingon, Mass.)) were injected sub-cutaneously with 30 mg/kg of ISIS 401025 (5-10-5 MOE gapmer prothromin antisense) in a volume of 200 ml of saline or with 200 ml of saline (antisense control) twice per week for three weeks (total of 6 injections).

Two days after the second injection, the mice were divided into 7 groups and treated as summarized in Table 5, below. All injections were subcutaneous and in a total volume of 200 µl of sterile saline.

TABLE 5

Prothrombin antisense and antidote compounds

| Group | Treatment | Description |
|---|---|---|
| 1 | Single injection of 30 mg/kg of 405277 | 5-10-5 MOE gap antidote |
| 2 | Single injection of 60 mg/kg of 405277 | 5-10-5 MOE gap antidote |
| 3 | Single injection of 90 mg/kg of 405277 | 5-10-5 MOE gap antidote |
| 4 | Single injection of 30 mg/kg of 405278 | Uniform MOE antidote |
| 5 | Single injection of 60 mg/kg of 405278 | Uniform MOE antidote |
| 6 | Single injection of 90 mg/kg of 405278 | Uniform MOE antidote |
| 7 | Single injection of saline | Antidote control |

Example 9

Sample Collection

Three days after antidote (or saline control) treatment, platelet poor plasma (PPP) was collected by cardiac puncture, as follows. Mice were anesthetized and a 27 gage needle attached to a 1 ml syringe preloaded with 65 µl of buffered citrate (0.06 Molar sodium citrate, pH 7.4) was inserted between the ribs and into the heart. 0.6 ml of blood was quickly withdrawn, resulting in a final ratio of nine parts whole blood to one part citrate buffer. Mice were euthanized. The needle was removed from the syringe and the blood/citrate buffer sample was emptied into a plastic tube with a cap. That sample was immediately mixed by tapping and inverting the capped tube. Within four hours of cardiac puncture, the sample was centrifuged at 2000 rcg for 15 minutes at 22° C. and the top rough plasma was removed and placed in a new tube. That rough plasma was centrifuged a second time, and the top layer was removed and placed in a new tube. That PPP sample was aliquoted and stored at −80° C.

Immediately after euthinization, livers were collected and total RNA was isolated from the livers using Rneasy mini kit (Quiagen).

Example 10

Prothrombin RNA

Figure 6:
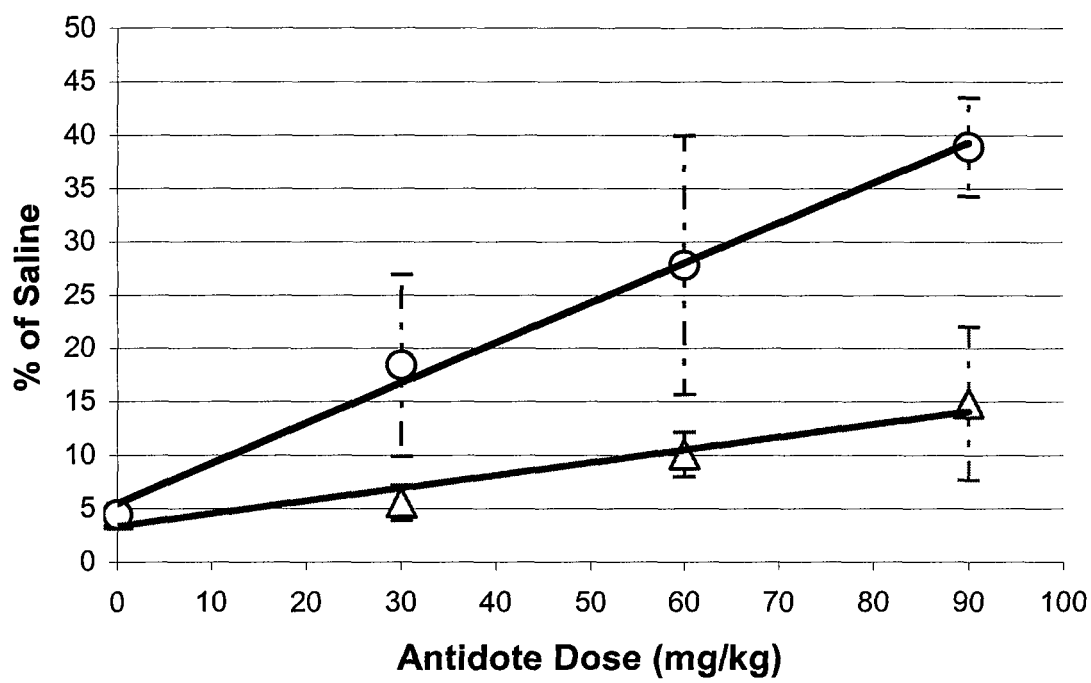
FIG. 6 shows total prothrombin RNA from livers of mice at 3 days following antisense and antidote treatment as described in Example 10. Data are expressed as percent of saline treated (antisense control). Zero on the X-axis represents no antidote (antidote control).

Total RNA from the livers (Example 9) were analyzed by RT-PCR. The forward primer for those reactions was: AAGG-GAATTTGGCTGTGACAA (SEQ ID NO. 9) and the reverse primer was: ACTTGGGTCCCCCTGCCTGCCX (SEQ ID NO. 10). Results are shown in FIG. 6.

Example 11

Thrombin Generation

Figure 7:
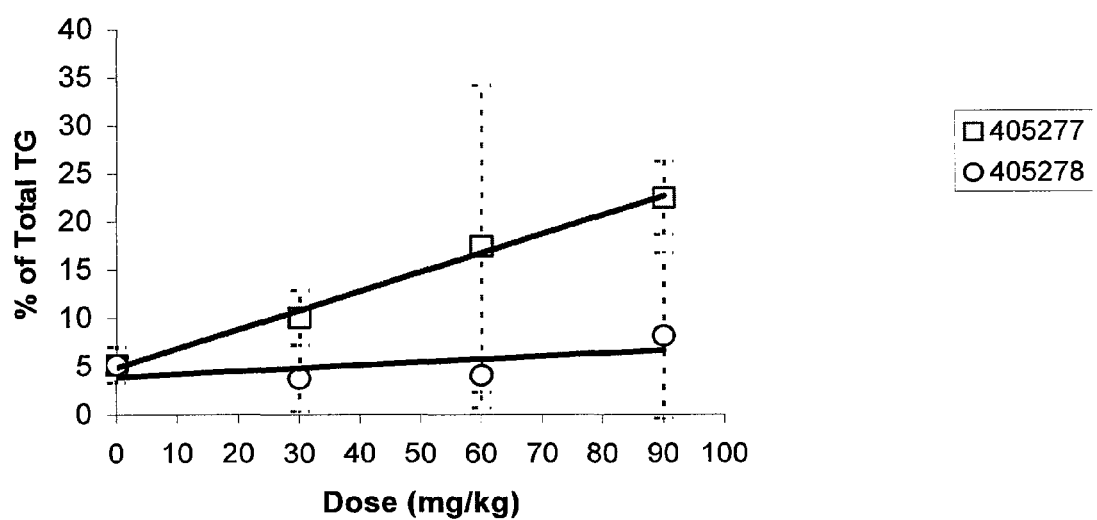
FIG. 7 shows total thrombin generation three days after treatment with antidote or with control oligonucleotide as described in Example 11.

Platelet poor plasma samples from Example 9 were diluted 1:2 with saline and thrombin generation was measured using by Thrombin Generation Assay (TGA) using a Technothrombin TGA kit (Technoclone, Vienna Austria) following manufacturers instructions. Results are shown in FIG. 7.

Example 12

Prothrombin Time (PT)/Activated Partial Thromboplastin Time (aPTT)

Figure 8:
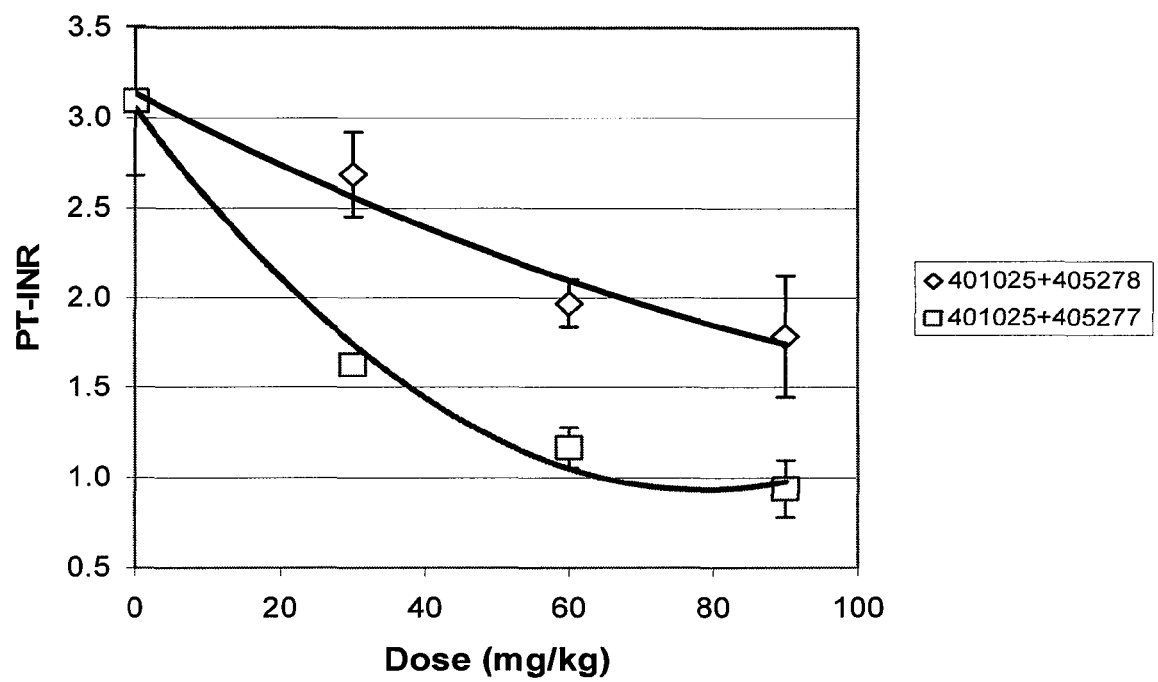
FIG. 8 shows results of prothrombin time (PT-INR) calculations described in Example 12.
Figure 9:
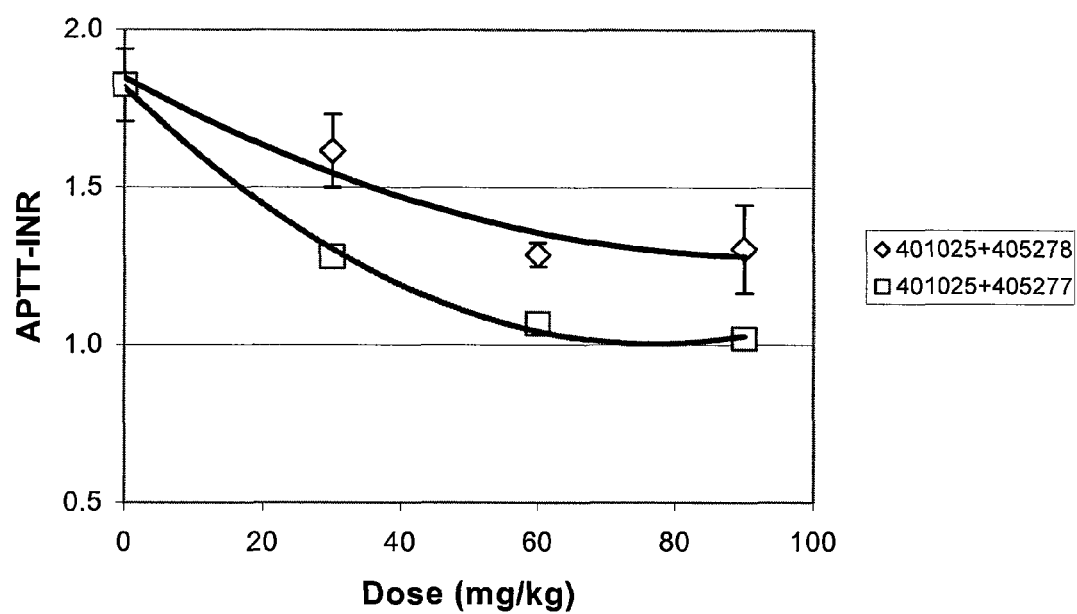
FIG. 9 shows results of activated partial thromboplastin time (aPPT) calculations described in Example 12.

Mouse PPP samples were assayed for PT and aPTT using an ACL 1000 coagulation analyzer (IL Instrumentation, Beckman Coulter, Fullerton, Calif.) at 37° C. The PT tests were initiated using thromboplastin (Dade Thromboplastin C Plus, Dade Behring Marburg GmbH, Germany) and the aPTT tests were performed by adding ellagic acid mixture (APTT-XL, Pacific Hemostasis, Fisher Diagnosis, Middletown Va.) and CaCl2. Pooled values obtained from the mice treated with saline were used as basal PT and aPTT. PT INR was calculated according to: INR=(PT/baseline PT)ISI, where ISI is the international sensitivity index of the thromboplastin used. Relative aPTT was calculated by dividing the measured values by baseline values. Results are shown in FIGS. 8 and 9.

Example 13

Specificity of Prothrombin Antidote Effect

To test the sequence-specificity of the observed antidote effect, the same antidote compounds were tested for their ability to restore prothrombin following treatment with a non-complementary antisense compound that also targets prothrombin. Compounds are summarized in Table 6, below.

TABLE 6

Prothrombin antisense and non-corresponding antidote compounds

| ISIS # | Chemistry Motif | Sequence | Description | SEQ ID |
|---|---|---|---|---|
| 401029 | 5-10-5 MOE gap | GACAATCACTTTTATTGAGA | Prothrombin antisense | 11 |
| 405277 | 5-10-5 MOE gap | AAGGACCTACACTATGGAAT | Antidote to 401025 | 8 |
| 405278 | Uniform MOE | AAGGACCTACACTATGGAAT | Antidote to 401025 | 8 |

Figure 10:
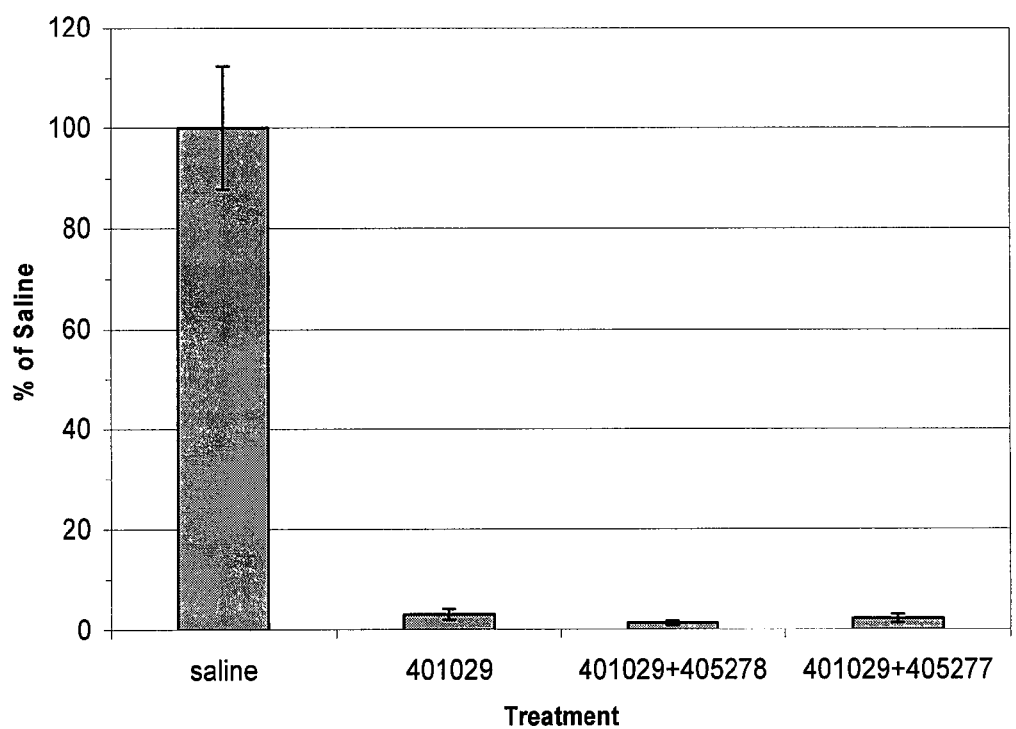
FIG. 10 shows the total prothrombin RNA three days after injection of non-complementary antidotes as described in Example 10. Results demonstrate the specificity of antidote activity.

Mice were treated and samples were obtained and assayed as described above (Examples 8-12). The single sub-cutaneous injections of 90 mg/kg of antidote compounds capable of reversing the antisense activity of antisense compound 401025 (to which they are complementary) did not reverse the antisense effect of non-complementary antisense compound 401029. Results for prothrombin RNA are shown in FIG. 10. Similar results were obtained for PT-INR.

Example 14

Toxicity Studies

Toxicity of antidotes ISIS-403277 and 403728 was assessed by testing serum from animals treated with those compounds for known markers of toxicity. The toxicity profile of those compounds was similar to those previously observed for similarly modified oligonucleotides.

Example 15

In Vivo Sense-Oligonucleotide-Antidote for Antisense Inhibition of Murine Factor XI in BALB/c Mice Oligonucleotides In a second cohort, ISIS 404071 (antisense compound targeted to Factor XI) was administered subcutaneously to BALB/c mice twice a week for three weeks at a dose of 40 mg/kg. Forty-eight hours after the final treatment of ISIS 404071, a single injection of 90 mg/kg of ISIS 418026 (Antidote complementary to ISIS 404071) was administered.

In a third cohort, ISIS 404057 (antisense compound targeted to Factor XI) was administered subcutaneously to BALB/c mice twice a week for three weeks at a dose of 40 mg/kg. Forty-eight hours after the final treatment of ISIS 404057, a single injection of PBS was administered subcutaneously.

In a fourth cohort, ISIS 404057 (antisense compound targeted to Factor XI) was administered subcutaneously to BALB/c mice twice a week for three weeks at a dose of 40 mg/kg. Forty-eight hours after the final treatment of ISIS 404057, a single injection of 90 mg/kg of ISIS 418026 (Antidote complementary to ISIS 404071) was administered.

Following antidote or PBS administration, a set of 4 mice from each cohort were sacrificed at 12 hours, 1 day, 2 days, 3 days, 7 days, and 14 days. Whole liver was collected for RNA analysis and PPP was collected for aPTT analysis.

RNA Analysis

RNA was extracted from liver tissue for real-time PCR analysis of Factor XI. Results are presented as percent inhibition of Factor XI, relative to PBS control. As shown in Table

| ISIS # | Chemistry Motif | Sequence | Description | SEQ ID |
|---|---|---|---|---|
| 404071 | 5-10-5 MOE gap all PS | TGGTAATCCACTTTCAGAGG | Antisense targeting Factor XI | 12 |
| 404057 | 5-10-5 MOE gap all PS | TCCTGGCATTCTCGAGCATT | Antisense targeting Factor XI | 13 |
| 418026 | 5-10-5 MOE gap all PS | CCTCTGAAAGTGGATTACCA | Antidote to 404071 | 14 |

Treatment

The effects of antisense compounds directed to Factor XI and an antidote were tested in BALB/c mice. In a first cohort, ISIS 404071 (antisense compound targeted to Factor XI) was administered subcutaneously to BALB/c mice twice a week for three weeks at a dose of 40 mg/kg. Forty-eight hours after the final treatment of ISIS 404071, a single injection of PBS was administered subcutaneously.

7, mice treated with ISIS 404071 without antidote showed progressive decrease in inhibition over the 14 day observation period. However, mice treated with ISIS 404071 and its antidote (ISIS 418026) showed an accelerated decrease in inhibition over the 14 day observation period in comparison to mice which did not receive antidote. Also shown in Table 7, treatment with ISIS 418026 did not accelerate the decrease in the antisense activity of ISIS 404057.

TABLE 7

Percent inhibition of mouse Factor XI mRNA compared to PBS control

|  | 12 hours | 1 day | 2 days | 3 days | 7 days | 14 days |
|---|---|---|---|---|---|---|
| ISIS 404071 | 93 | 90 | 89 | 88 | 81 | 67 |
| ISIS 404071 + ISIS 418026 | 90 | 87 | 72 | 66 | 57 | 31 |
| ISIS 404057 | n.d. | n.d. | n.d. | 95 | n.d. | n.d. |
| ISIS 404057 + ISIS 418026 | n.d. | n.d. | n.d. | 97 | n.d. | n.d. | nd = no data aPTT Assay

As shown in Table 8, mice treated with ISIS 404071 and antidote (ISIS 418026) showed progressive decrease of aPTT over the 14 day observation period compared to mice treated with ISIS 404071 without antidote.

TABLE 8

Effect of antidote treatment on aPTT INR

|  | 12 hours | 1 day | 2 day | 3 day | 7 day | 14 day |
|---|---|---|---|---|---|---|
| ISIS 404071 | 1.51 | 1.30 | 1.35 | 1.27 | 1.18 | 1.05 |
| ISIS 404071 + ISIS 418026 | 1.45 | 1.23 | 1.16 | 1.15 | 1.10 | 0.95 |

Example 16

In Vivo Factor VIIa Protein-Antidote for Antisense Inhibition of Murine Factor XI in BALB/c Mice Treatment The effect of human Factor VIIa protein as a non-oligomeric antidote for ISIS 404071 was tested in BALB/c mice. Two experimental groups of BALB/c mice were treated with 20 mg/kg of ISIS 404071, administered subcutaneously twice a week for 3 weeks. Two control groups of BALB/c mice were treated with PBS, administered subcutaneously twice a week for 3 weeks. Thrombus formation was induced with $FeCl_3$ in all of the mice except the first control group. Fifteen minutes before $FeCl_3$ treatment, the first experimental group was treated with 5 µg/kg of human Factor VIIa protein antidote (product no. 407act, American Diagnostica Inc.). Two days after their last dose, all mice were anesthetized with 150 mg/kg of ketamine mixed with 10 mg/kg of xylazine administered by intraperitoneal injection.

In mice undergoing $FeCl_3$ treatment, thrombus formation was induced by applying a piece of filter paper (2×4 mm) pre-saturated with 10% $FeCl_3$ solution directly on the vena cava. After 3 minutes of exposure, the filter paper was removed. Thirty minutes after the filter paper application, a fixed length of the vein containing the thrombus was dissected out for platelet analysis.

Quantification of Platelet Composition

Real-time PCR quantification of platelet factor-4 (PF-4) was used to quantify platelets in the vena cava as a measure of thrombus formation. Results are presented as a percentage of PF-4 in antidote treated and untreated mice, as compared to the two PBS-treated control groups. As shown in Table 9, animals treated with human Factor VIIa protein antidote expressed more PF-4 in comparison to animals treated with ISIS 404071 alone. These data indicate that human Factor VIIa is successful in rescuing the effect of antisense oligonucleotide inhibition.

TABLE 9

Analysis of thrombus formation by real-time PCR quantification of PF-4 in the $FeCl_3$ induced venous thrombosis model

| Treatment | PF-4 |
|---|---|
| PBS − $FeCl_3$ | 0 |
| PBS + $FeCl_3$ | 100 |
| ISIS 404071 | 18 |
| ISIS 404071 + hFV7a | 68 |

The invention claimed is:

1. A method of reducing the activity of an antisense compound comprising identifying an animal that has received an antisense compound and administering to said animal an antidote compound comprising a modified oligonucleotide consisting of 12 to 30 linked nucleosides and having a nucleobase sequence complementary to said antisense compound.

2. The method of claim 1, wherein the animal is a human.

3. A method of inhibiting antisense activity in a cell comprising contacting the cell with an antidote compound comprising a modified oligonucleotide consisting of 12 to 30 linked nucleosides and having a nucleobase sequence complementary to an antisense compound and thereby inhibiting the antisense activity in the cell.

4. The method of claim 3, wherein the cell is in an animal.

5. The method of claim 4, wherein the animal is a human.

6. A method comprising:
contacting a cell with an antisense compound;
detecting antisense activity; and
contacting the cell with an antidote compound.

7. The method of claim 6, wherein the antidote compound comprises a modified oligonucleotide consisting of 12 to 30 linked nucleosides and having a nucleobase sequence complementary to said antisense compound.

8. The method of claim 6, wherein the detecting antisense activity comprises measuring a parameter selected from the group consisting of an amount of target mRNA present, an amount of target protein present, and an activity of a target protein.

9. A method of ameliorating a side-effect of antisense treatment comprising:
   contacting a cell with an antisense compound;
   detecting a side-effect;
   contacting the cell with an antidote compound; and
   thereby ameliorating the side effect of the antisense compound.

10. The method of claim 9, wherein the antidote compound comprises a modified oligonucleotide consisting of 12 to 30 linked nucleosides and having a nucleobase sequence complementary to said antisense compound.

11. A method of treating a patient comprising:
    administering to the patient an antisense compound;
    monitoring the patient for antisense activity; and
    if the antisense activity becomes higher than desired, administrating an antidote compound.

12. The method of claim 11, wherein the antidote compound comprises a modified oligonucleotide consisting of 12 to 30 linked nucleosides and having a nucleobase sequence complementary to said antisense compound.

13. The method of claim 11, wherein the monitoring antisense activity comprises measuring a parameter selected from the group consisting of an amount of target mRNA present, an amount of target protein present, and an activity of a target protein.

14. The method of claim 11 further comprising detecting antidote activity by measuring antisense activity after administration of the antidote compound.

15. The method of claim 11, wherein the patient is a human.

16. A method of treating a patient comprising:
    administering to the patient an antisense compound;
    monitoring the patient for one or more side effect; and
    if the one or more side effect reaches an undesirable level, administrating an antidote compound.

17. The method of claim 16, wherein the antidote compound comprises a modified oligonucleotide consisting of 12 to 30 linked nucleosides and having a nucleobase sequence complementary to said antisense.

18. The method of claim 16, wherein the patient is a human.

* * * * *

UNITED STATES PATENT AND TRADEMARK OFFICE
CERTIFICATE OF CORRECTION

PATENT NO. : 8,389,488 B2  Page 1 of 1
APPLICATION NO. : 12/740974
DATED : March 5, 2013
INVENTOR(S) : Monia et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 174 days.

Signed and Sealed this

First Day of September, 2015

Michelle K. Lee
*Director of the United States Patent and Trademark Office*

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1
tccagcactt tctttccgg            20

<210> SEQ ID NO 2
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 2
ccggaaaaga aagtgctgga            20

```
<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 3
tcgatctcct tttatgcccg                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 4
ctgctagcct ctggatttga                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 5
tcaaatccag aggctagcag                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 6
ccggaaaaga aagtgctgga                                              20

<210> SEQ ID NO 7
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 7
attccatagt gtaggcctt                                               19

<210> SEQ ID NO 8
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 8
aaggacctac actatggaat                                              20

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
```

```
aagggaattt ggctgtgaca a                                              21

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
acttgggtcc ccctgcctgc c                                              21

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 11
gacaatcact tttattgaga                                                20

<210> SEQ ID NO 12
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 12
tggtaatcca ctttcagagg                                                20

<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 13
tcctggcatt ctcgagcatt                                                20

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 14
cctctgaaag tggattacca                                                20
```